United States Patent
Dauphinee et al.

(10) Patent No.: US 11,603,398 B2
(45) Date of Patent: Mar. 14, 2023

(54) INTESTINAL EXPRESSION OF PROGRAMMED DEATH LIGAND 1

(71) Applicant: ENGENE, INC., Montreal (CA)

(72) Inventors: Shauna Marie Dauphinee, Montreal (CA); Connor Daniel Alexander McCarthy, Montreal (CA); Jeremy Dupaul-Chicoine, Montreal (CA); Eric Hsu, Vancouver (CA); Ghania Chikh, Ottawa (CA); Anthony Cheung, Montreal (CA)

( * ) Notice: Subject to any disclaimer, the term of this patent is extended or adjusted under 35 U.S.C. 154(b) by 154 days.

(21) Appl. No.: 16/348,834

(22) PCT Filed: Nov. 9, 2017

(86) PCT No.: PCT/CA2017/051340
§ 371 (c)(1),
(2) Date: May 9, 2019

(87) PCT Pub. No.: WO2018/085935
PCT Pub. Date: May 17, 2018

(65) Prior Publication Data
US 2019/0263887 A1    Aug. 29, 2019

Related U.S. Application Data

(60) Provisional application No. 62/419,899, filed on Nov. 9, 2016.

(51) Int. Cl.
| | | |
|---|---|---|
| C07K 14/705 | (2006.01) | |
| A61K 9/51 | (2006.01) | |
| C12N 15/85 | (2006.01) | |
| A61P 1/00 | (2006.01) | |
| A61P 37/06 | (2006.01) | |
| A61P 1/04 | (2006.01) | |
| A61K 31/711 | (2006.01) | |
| A61P 1/06 | (2006.01) | |
| C12Q 1/6883 | (2018.01) | |

(52) U.S. Cl.
CPC ...... *C07K 14/70532* (2013.01); *A61K 9/5161* (2013.01); *A61K 31/711* (2013.01); *A61P 1/00* (2018.01); *A61P 1/04* (2018.01); *A61P 1/06* (2018.01); *A61P 37/06* (2018.01); *C12N 15/85* (2013.01); *C12Q 1/6883* (2013.01); *C07K 2319/30* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 2009/0110667 A1* | 4/2009 | Mozaffarian | ........... | A61P 19/02 424/93.7 |
| 2010/0035973 A1* | 2/2010 | Walker | ................... | C12N 15/86 514/44 R |
| 2011/0171314 A1* | 7/2011 | Cheung | ..................... | A61P 3/10 435/325 |
| 2011/0178030 A1* | 7/2011 | Sun | .......................... | A61P 29/00 514/21.2 |
| 2012/0076805 A1* | 3/2012 | Sharpe | .................... | A61K 35/17 424/184.1 |
| 2012/0164174 A1* | 6/2012 | Sung | ...................... | A61K 39/12 424/277.1 |
| 2012/0282343 A1* | 11/2012 | Leong | .................. | A61K 9/5161 977/773 |
| 2012/0295355 A1* | 11/2012 | Baker | ................ | A61K 48/0041 536/20 |
| 2013/0130965 A1* | 5/2013 | Petri, Jr. | ............ | G01N 33/6893 514/1.1 |
| 2014/0341933 A1* | 11/2014 | Riley | ..................... | A61K 35/17 424/184.1 |
| 2015/0139994 A1* | 5/2015 | Xu | .......................... | A61K 35/32 424/134.1 |
| 2016/0220636 A1* | 8/2016 | Bacus | .................. | A61K 9/0014 |
| 2016/0235683 A1* | 8/2016 | Powell | ............... | A61K 49/0002 |
| 2016/0304851 A1* | 10/2016 | Schüttrumpf | ............. | A61P 7/04 |
| 2017/0189476 A1* | 7/2017 | Sung | .................. | A61K 39/0005 |
| 2018/0214487 A1* | 8/2018 | Fiorina | .............. | C07K 16/2818 |

FOREIGN PATENT DOCUMENTS

WO    WO 2011060218 A1    5/2011

OTHER PUBLICATIONS

Keir et al. Annu. Rev. Immunol. 2008. 26: 677-704.*
Al-Chaqmaqchi, H. et al, "The Role of Programmed Cell Death Ligand-1 (PD-L1/ CD 274) in the Development of Graft versus Host Disease", PLoS One, vol. 8, No. 4, p. e60367 (2013).
Blazar et al, "Blockade of Programmed Death-1 Engagement Accelerates Graft-Versus-Host Disease Lethality by IFN-γ-Dependent Mechanizm", J. of Immunol., vol. 171, pp. 1272-1277 (2003).
Deng et al, "B7H1/CD80 Interactioin Augments PD-1-Dependent T Cell Apoptosis and Ameliorates Graft-versuss-Host Disease", J. of Immunol., vol. 194, pp. 560-174 (2015).
Song et al., "Protective effects of Fc-fused PD-L1 on two different animal models of colitis", Gut, vol. 64, No. 2, pp. 260-271 (2015).

(Continued)

*Primary Examiner* — Ilia I Ouspenski
(74) *Attorney, Agent, or Firm* — Todd Lorenz

(57) ABSTRACT

Provided herein are methods and compositions for the amelioration of inflammatory disorders comprising the intestinal expression of programmed death ligand 1.

12 Claims, 23 Drawing Sheets

Specification includes a Sequence Listing.

(56) References Cited

OTHER PUBLICATIONS

Patsoukis et al., "Selective Effect of PDF-1 on Akt and Ras Pathways Regulate Molecular Components of the Cell Cycle and Inhibit T Cell Profliferation", Sci. Signal, vol. 5 (2012).

Spagnuolo et al., "Involvement of Immunie Regulation in Mulitple Sclerosis", Imunolgoy and immunogenetics Insights, vol. 9, pates 1-10 (2017).

* cited by examiner pVAX_hPD-L1
GGATCTAGGTGAAGATCCTTTTTGATAATCTCATGACCAAAATCCCTTAACGTGAGTTTTCGTTCCACTGAGCGTCAGAC
CCCGTAGAAAAGATCAAAGGATCTTCTTGAGATCCTTTTTTTCTGCGCGTAATCTGCTGCTTGCAAACAAAAAAACCACC
GCTACCAGCGGTGGTTTGTTTGCCGGATCAAGAGCTACCAACTCTTTTTCCGAAGGTAACTGGCTTCAGCAGAGCGCAGA
TACCAAATACTGTCCTTCTAGTGTAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGGGTTGGACTCAAGACGATAGTTACC
GGATAAGGCGCAGCGGTCGGGCTGAACGGGGGGTTCGTGCACACAGCCCAGCTTGGAGCGAACGACCTACACCGAACTGA
GATACCTACAGCGTGAGCTATGAGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATGGAAAAACGCCAGCAACGCGGCCTTTTTAC
GGTTCCTGGCCTTTTGCTGGCCTTTTGCTCACATGTTCTTGACTCTTCGCGATGTACGGGCCAGATATACGCGTTGACAT
TGATTATTGACTAGTTATTAATAGTAATCAATTACGGGGTCATTAGTTCATAGCCCATATATGGAGTTCCGCGTTACATA
ACTTACGGTAAATGGCCCGCCTGGCTGACCGCCCAACGACCCCCGCCCATTGACGTCAATAATGACGTATGTTCCCATAG
TAACGCCAATAGGGACTTTCCATTGACGTCAATGGGTGGACTATTTACGGTAAACTGCCCACTTGGCAGTACATCAAGTG
TATCATATGCCAAGTACGCCCCCTATTGACGTCAATGACGGTAAATGGCCCGCCTGGCATTATGCCCAGTACATGACCTT
ATGGGACTTTCCTACTTGGCAGTACATCTACGTATTAGTCATCGCTATTACCATGGTGATGCGGTTTTGGCAGTACATCA
ATGGGCGTGGATAGCGGTTTGACTCACGGGGATTTCCAAGTCTCCACCCCATTGACGTCAATGGGAGTTTGTTTTGGCAC
CAAAATCAACGGGACTTTCCAAAATGTCGTAACAACTCCGCCCCATTGACGCAAATGGGCGGTAGGCGTGTACGGTGGGA
GGTCTATATAAGCAGAGCTCTCTGGCTAACTAGAGAACCCACTGCTTACTGGCTTATCGAAATTAATACGACTCACTATA
GGGAGACCCAAGCTGGCTAGCGTTTAAACTT<u>AAGCTTCCACCATGAGAATCTTCGCGGTGTTCATCTTCATGACCTACTG</u>
<u>GCACCTCCTGAACGCTTTCACTGTGACCGTGCCTAAGGACCTCTACGTCGTGGAATACGGCTCCAACATGACCATCGAGT</u>
<u>GCAAATTCCCAGTGGAGAAGCAGCTGGACCTGGCTGCCCTGATCGTGTACTGGGAAATGGAGGACAAGAACATCATCCAA</u>
<u>TTCGTGCATGGGGAGGAGGACCTGAAGGTCCAGCATTCGTCATATCGGCAAAGAGCCAGGCTGCTGAAGGATCAGCTGTC</u>
<u>CCTCGGCAATGCGGCACTGCAGATTACCGATGTGAAGCTGCAGGACGCCGGAGTCTACCGGTGCATGATTTCCTACGGCG</u>
<u>GAGCAGACTACAAGCGCATTACCGTGAAGGTCAACGCTCCCTACAACAAGATCAACCAGCGGATTCTGGTGGTCGACCCT</u>
<u>GTGACCTCCGAGCATGAGCTGACCTGTCAAGCCGAAGGTTACCCGAAAGCGGAAGTGATCTGGACGTCGAGCGACCACCA</u>
<u>GGTCTTGAGCGGAAAGACGACCACTACTAACAGCAAGCGGGAAGAGAAACTGTTTAACGTGACCAGCACTCTTCGGATCA</u>
<u>ACACCACCACTAACGAGATTTTCTACTGTACCTTTCGCCGGCTTGACCCGGAAGAAAATCACACCGCCGAGCTCGTGATC</u>
<u>CCCGAGCTGCCCCTCGCCCACCCTCCTAACGAAAGAACCCACCTGGTCATCTTGGGGGCCATCCTGCTGTGCCTGGGAGT</u>
<u>GGCCCTGACCTTCATTTTTAGGCTCCGAAAGGGCCGCATGATGGACGTGAAGAAATGCGGAATCCAGGACACTAACTCCA</u>
<u>AGAAGCAGTCCGATACTCACCTGGAAGAAACCTAGGAATTCCAGCACAGTGGCGGCCGCTCGAGTCTAGAGGGCCCGTTT</u>
AAACCCGCTGATCAGCCTCGACTGTGCCTTCTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGGCATGCTGGGGATGCGGTGGGCT
CTATGGCTTCTACTGGGCGGTTTTATGGACAGCAAGCGAACCGGAATTGCCAGCTGGGGCGCCCTCTGGTAAGGTTGGGA
AGCCCTGCAAAGTAAACTGGATGGCTTTCTCGCCGCCAAGGATCTGATGGCGCAGGGGATCAAGCTCTGATCAAGAGACA
GGATGAGGATCGTTTCGCATGATTGAACAAGATGGATTGCACGCAGGTTCTCCGGCCGCTTGGGTGGAGAGGCTATTCGG
CTATGACTGGGCACAACAGACAATCGGCTGCTCTGATGCCGCCGTGTTCCGGCTGTCAGCGCAGGGGCGCCCGGTTCTTT
TTGTCAAGACCGACCTGTCCGGTGCCCTGAATGAACTGCAAGACGAGGCAGCGCGGCTATCGTGGCTGGCCACGACGGGC
GTTCCTTGCGCAGCTGTGCTCGACGTTGTCACTGAAGCGGGAAGGGACTGGCTGCTATTGGGCGAAGTGCCGGGGCAGGA
TCTCCTGTCATCTCACCTTGCTCCTGCCGAGAAAGTATCCATCATGGCTGATGCAATGCGGCGGCTGCATACGCTTGATC
CGGCTACCTGCCCATTCGACCACCAAGCGAAACATCGCATCGAGCGAGCACGTACTCGGATGAAGCCGGTCTTGTCGAT
CAGGATGATCTGGACGAAGAGCATCAGGGGCTCGCGCCAGCCGAACTGTTCGCCAGGCTCAAGGCGAGCATGCCCGACGG
CGAGGATCTCGTCGTGACCCATGGCGATGCCTGCTTGCCGAATATCATGGTGGAAAATGGCCGCTTTTCTGGATTCATCG
ACTGTGGCCGGCTGGGTGTGGCGGACCGCTATCAGGACATAGCGTTGGCTACCCGTGATATTGCTGAAGAGCTTGGCGGC
GAATGGGCTGACCGCTTCCTCGTGCTTTACGGTATCGCCGCTCCCGATTCGCAGCGCATCGCCTTCTATCGCCTTCTTGA
CGAGTTCTTCTGAATTATTAACGCTTACAATTTCCTGATGCGGTATTTTCTCCTTACGCATCTGTGCGGTATTTCACACC
GCATACAGGTGGCACTTTTCGGGGAAATGTGCGCGGAACCCCTATTTGTTTATTTTTCTAAATACATTCAAATATGTATC
CGCTCATGAGACAATAACCCTGATAAATGCTTCAATAATAGCACGTGCTAAAACTTCATTTTTAATTTAAAA

FIG.1 pVax_hPD-L1-Fc
```
GGATCTAGGTGAAGATCCTTTTTGATAATCTCATGACCAAAATCCCTTAACGTGAGTTTTCGTTCCACTGAGCGTCAGAC
CCCGTAGAAAAGATCAAAGGATCTTCTTGAGATCCTTTTTTTCTGCGCGTAATCTGCTGCTTGCAAACAAAAAAACCACC
GCTACCAGCGGTGGTTTGTTTGCCGGATCAAGAGCTACCAACTCTTTTTCCGAAGGTAACTGGCTTCAGCAGAGCGCAGA
TACCAAATACTGTCCTTCTAGTGTAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGGGTTGGACTCAAGACGATAGTTACC
GGATAAGGCGCAGCGGTCGGGCTGAACGGGGGGTTCGTGCACACAGCCCAGCTTGGAGCGAACGACCTACACCGAACTGA
GATACCTACAGCGTGAGCTATGAGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAGTCCTGTCGGGTTTCGCCACCT
CTGACTTGAGCGTCGATTTTTGTGATGCTCGTCAGGGGGCGGAGCCTATGGAAAAACGCCAGCAACGCGGCCTTTTTAC
GGTTCCTGGCCTTTTGCTGGCCTTTTGCTCACATGTTCTTGACTCTTCGCGATGTACGGGCCAGATATACGCGTTGACAT
TGATTATTGACTAGTTATTAATAGTAATCAATTACGGGGTCATTAGTTCATAGCCCATATATGGAGTTCCGCGTTACATA
ACTTACGGTAAATGGCCCGCCTGGCTGACCGCCCAACGACCCCCGCCCATTGACGTCAATAATGACGTATGTTCCCATAG
TAACGCCAATAGGGACTTTCCATTGACGTCAATGGGTGGACTATTTACGGTAAACTGCCCACTTGGCAGTACATCAAGTG
TATCATATGCCAAGTACGCCCCCTATTGACGTCAATGACGGTAAATGGCCCGCCTGGCATTATGCCCAGTACATGACCTT
ATGGGACTTTCCTACTTGGCAGTACATCTACGTATTAGTCATCGCTATTACCATGGTGATGCGGTTTTGGCAGTACATCA
ATGGGCGTGGATAGCGGTTTGACTCACGGGGATTTCCAAGTCTCCACCCCATTGACGTCAATGGGAGTTTGTTTTGGCAC
CAAAATCAACGGGACTTTCCAAAATGTCGTAACAACTCCGCCCCATTGACGCAAATGGGCGGTAGGCGTGTACGGTGGGA
GGTCTATATAAGCAGAGCTCTCTGGCTAACTAGAGAACCCACTGCTTACTGGCTTATCGAAATTAATACGACTCACTATA
GGGAGACCCAAGCTGGCTAGCGTTTAAACTTAAGCTTCCACCATGAGAATCTTCGCGGTGTTCATCTTCATGACCTACTG
GCACCTCCTGAACGCTTTCACTGTGACCGTGCCTAAGGACCTCTACGTCGTGGAATACGGCTCCAACATGACCATCGAGT
GCAAATTCCCAGTGGAGAAGCAGCTGGACCTGGCTGCCCTGATCGTGTACTGGGAAATGGAGGACAAGAACATCATCCAA
TTCGTGCATGGGGAGGAGGACCTGAAGGTCCAGCATTCGTCATATCGGCAAAGAGCCAGGCTGCTGAAGGATCAGCTGTC
CCTCGGCAATGCGGCACTGCAGATTACCGATGTGAAGCTGCAGGACGCCGGAGTCTACCGGTGCATGATTTCCTACGGCG
GAGCAGACTACAAGCGCATTACCGTGAAGGTCAACGCTCCCTACAACAAGATCAACCAGCGGATTCTGGTGGTCGACCCT
GTGACCTCCGAGCATGAGCTGACCTGTCAAGCCGAAGGTTACCCGAAAGCGGAAGTGATCTGGACGTCGAGCGACCACCA
GGTCTTGAGCGGAAAGACGACCACTACTAACAGCAAGCGGGAAGAGAAACTGTTTAACGTGACCAGCACTCTTCGGATCA
ACACCACCACTAACGAGATTTTCTACTGTACCTTTCGCCGGCTTGACCCGGAAGAAAATCACACCGCCGAGCTCGTGATC
CCCGAGCTGCCCCTCGCCCACCCTCCTAACGAAAGAACTCCCAAGTCTTGCGATAAGACCCACACATGCCCGCCATGCCC
AGCCCCGCCCGTGGCGGGCCCCTCCGTGTTTCTTTTCCCGCCGAAGCCTAAGGATACCCTGATGATCTCCCGCACCCCCG
AAGTCACTTGTGTGGTGGTGGACGTCAGCCACGAAGATCCGGAAGTCAAGTTCAATTGGTACGTGGACGGGGTCGAAGTG
CACAACGCCAAGACCAAGCCCCGCGAGGAACAGTACAACTCAACGTACCGGGTGGTGTCCGTGCTGACCGTGCTGCATCA
GGACTGGCTGAACGGAAAGGAGTACAAGTGCAAAGTGTCCAACAAGGGACTGCCGAGCTCGATCGAAAAGACCATTTCGA
AGGCCAAGGGGCAGCCTAGGGAGCCACAGGTCTATACCCTCCCGCCCTCACGAGATGAACTGACCAAGAACCAAGTGTCA
TTGACTTGCCTCGTGAAGGGCTTCTACCCTTCCGACATCGCCGTGGAATGGGAATCCAACGGACAGCCGGAGAACAACTA
CAAGACTACTCCGCCCGTGCTTGACTCCGACGGTTCGTTCTTCCTGTACTCCAAGCTGACCGTGGATAAGTCCCGCTGGC
AACAGGGCAACGTGTTCTCCTGCTCCGTGATGCACGAAGCCCTGCACAACCACTACACCCAGAAGTCCCTCTCGTTGAGC
CCTGGAAAATAGGAATTCCAGCACAGTGGCGGCCGCTCGAGTCTAGAGGGCCCGCGTTTAAACCCGCTGATCAGCCTCGACT
GTGCCTTCTAGTTGCCAGCCATCTGTTGTTTGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTCATTCTATTCTGGGGGGTGGGGTGGGCAGG
ACAGCAAGGGGGAGGATTGGGAAGACAATAGCAGGCATGCTGGGGATGCGGTGGGCTCTATGGCTTCTACTGGGCGGTTT
TATGGACAGCAAGCGAACCGGAATTGCCAGCTGGGGCGCCCTCTGGTAAGGTTGGGAAGCCCTGCAAAGTAAACTGGATG
GCTTTCTCGCCGCCAAGGATCTGATGGCGCAGGGGATCAAGCTCTGATCAAGAGACAGGATGAGGATCGTTTCGCATGAT
TGAACAAGATGGATTGCACGCAGGTTCTCCGGCCGCTTGGGTGGAGAGGCTATTCGGCTATGACTGGGCACAACAGACAA
TCGGCTGCTCTGATGCCGCCGTGTTCCGGCTGTCAGCGCAGGGGCGCCCGGTTCTTTTTGTCAAGACCGACCTGTCCGGT
GCCCTGAATGAACTGCAAGACGAGGCAGCGCGGCTATCGTGGCTGGCCACGACGGGCGTTCCTTGCGCAGCTGTGCTCGA
CGTTGTCACTGAAGCGGGAAGGGACTGGCTGCTATTGGGCGAAGTGCCGGGGCAGGATCTCCTGTCATCTCACCTTGCTC
CTGCCGAGAAAGTATCCATCATGGCTGATGCAATGCGGCGGCTGCATACGCTTGATCCGGCTACCTGCCCATTCGACCAC
CAAGCGAAACATCGCATCGAGCGAGCACGTACTCGGATGGAAGCCGGTCTTGTCGATCAGGATGATCTGGACGAAGAGCA
TCAGGGGCTCGCGCCAGCCGAACTGTTCGCCAGGCTCAAGGCGAGCATGCCCGACGGCGAGGATCTCGTCGTGACCCATG
GCGATGCCTGCTTGCCGAATATCATGGTGGAAAATGGCCGCTTTTCTGGATTCATCGACTGTGGCCGGCTGGGTGTGGCG
GACCGCTATCAGGACATAGCGTTGGCTACCCGTGATATTGCTGAAGAGCTTGGCGGCGAATGGGCTGACCGCTTCCTCGT
GCTTTACGGTATCGCCGCTCCCGATTCGCAGCGCATCGCCTTCTATCGCCTTCTTGACGAGTTCTTCTGAATTATTAACG
CTTACAATTTCCTGATGCGGTATTTTCTCCTTACGCATCTGTGCGGTATTTCACACCGCATACAGGTGGCACTTTTCGGG
GAAATGTGCGCGGAACCCCTATTTGTTTATTTTTCTAAATACATTCAAATATGTATCCGCTCATGAGACAATAACCCTGA
TAAATGCTTCAATAATAGCACGTGCTAAAACTTCATTTTTAATTTAAAA
```

FIG. 2

| Transfection | EC50 | Maximum ng/mg |
|---|---|---|
| 1 | 2.763 | 4065 |
| 2 | 2.166 | 5114 |
| 3 | 2.338 | 5767 |
| 4 | 2.546 | 6723 |

1 – Ladder
2 – Fc eluate 1
3 – Fc eluate 2
4 – Fc eluate 3
5 – Fc eluate 4
6 – PDL1-Fc eluate 1
7 – PDL1-Fc eluate 2
8 – PDL1-Fc eluate 3
9 – PDL1-Fc eluate 4
10 – recombinant PDL1-Fc

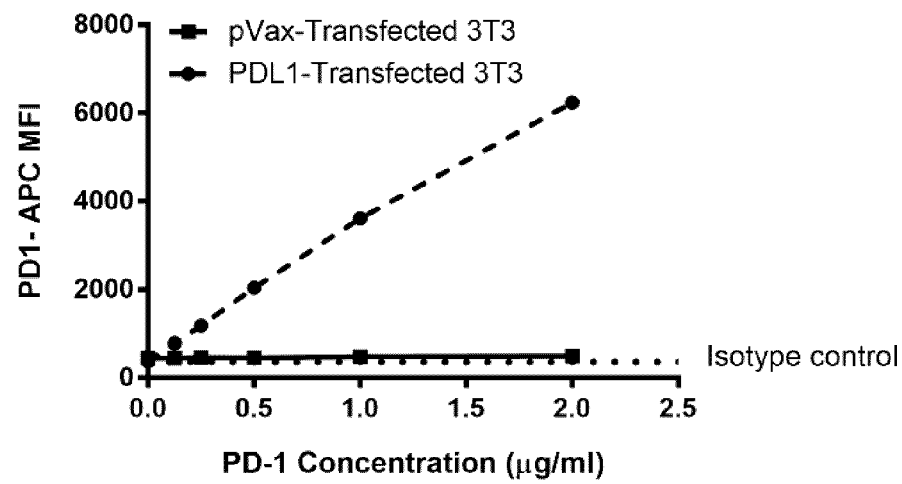
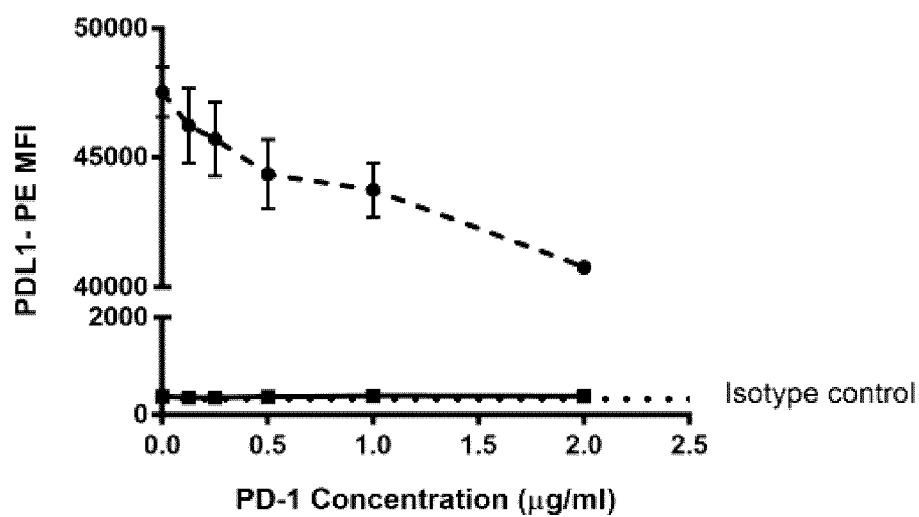
FIG. 7B

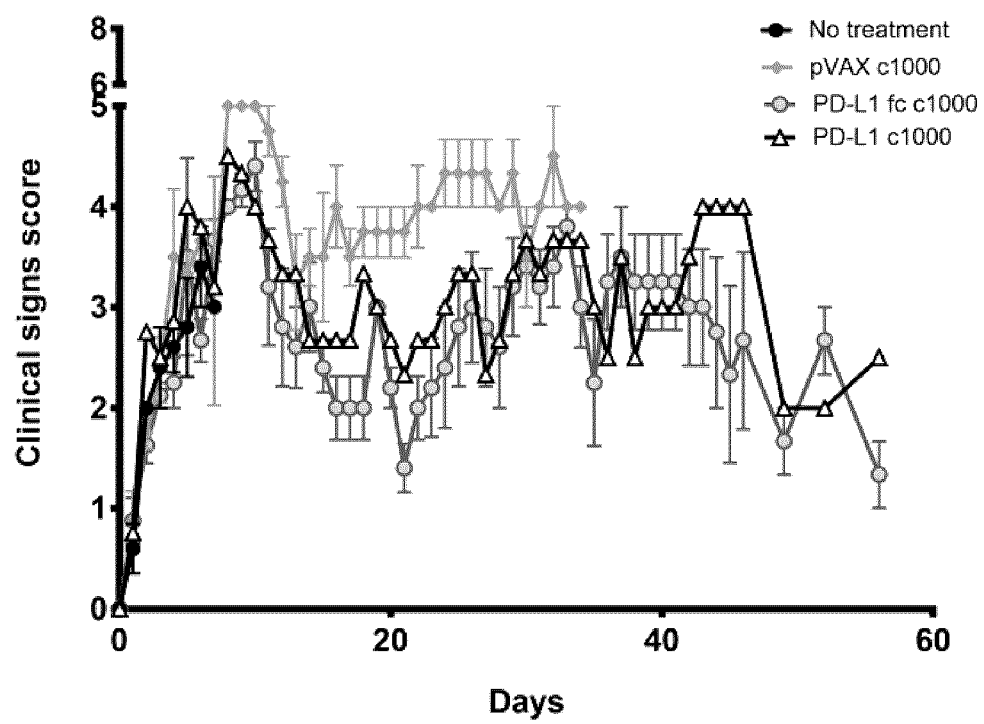
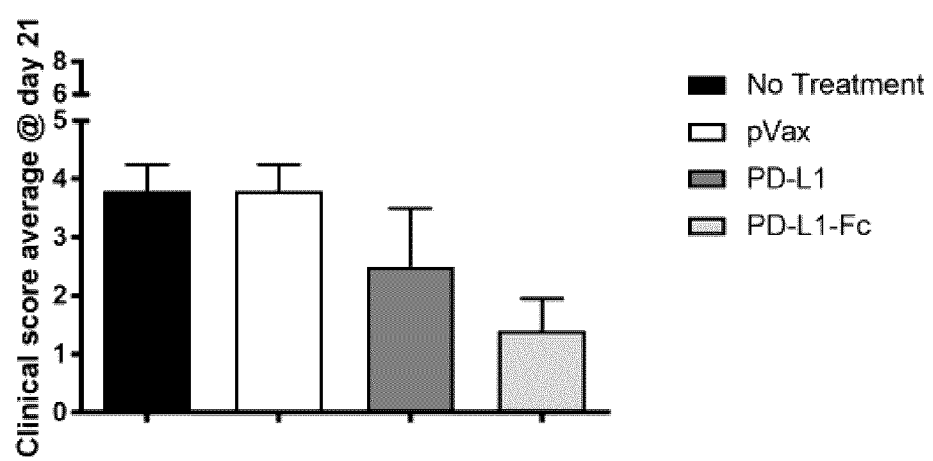
FIG. 9B

SEQUENCE LISTING

<160> NUMBER OF SEQ ID NOS: 8

<210> SEQ ID NO 1
<211> LENGTH: 290
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| Met | Arg | Ile | Phe | Ala | Val | Phe | Ile | Phe | Met | Thr | Tyr | Trp | His | Leu | Leu |
| 1 | | | | 5 | | | | | 10 | | | | | 15 | |
| Asn | Ala | Phe | Thr | Val | Thr | Val | Pro | Lys | Asp | Leu | Tyr | Val | Val | Glu | Tyr |
| | | | 20 | | | | | 25 | | | | | 30 | | |
| Gly | Ser | Asn | Met | Thr | Ile | Glu | Cys | Lys | Phe | Pro | Val | Glu | Lys | Gln | Leu |
| | | | 35 | | | | 40 | | | | | 45 | | | |
| Asp | Leu | Ala | Ala | Leu | Ile | Val | Tyr | Trp | Glu | Met | Glu | Asp | Lys | Asn | Ile |
| | 50 | | | | | 55 | | | | | 60 | | | | |
| Ile | Gln | Phe | Val | His | Gly | Glu | Glu | Asp | Leu | Lys | Val | Gln | His | Ser | Ser |
| 65 | | | | | 70 | | | | | 75 | | | | | 80 |
| Tyr | Arg | Gln | Arg | Ala | Arg | Leu | Leu | Lys | Asp | Gln | Leu | Ser | Leu | Gly | Asn |
| | | | | 85 | | | | | 90 | | | | | 95 | |
| Ala | Ala | Leu | Gln | Ile | Thr | Asp | Val | Lys | Leu | Gln | Asp | Ala | Gly | Val | Tyr |
| | | | 100 | | | | | 105 | | | | | 110 | | |
| Arg | Cys | Met | Ile | Ser | Tyr | Gly | Gly | Ala | Asp | Tyr | Lys | Arg | Ile | Thr | Val |
| | | | 115 | | | | 120 | | | | | 125 | | | |
| Lys | Val | Asn | Ala | Pro | Tyr | Asn | Lys | Ile | Asn | Gln | Arg | Ile | Leu | Val | Val |
| | 130 | | | | | 135 | | | | | 140 | | | | |
| Asp | Pro | Val | Thr | Ser | Glu | His | Glu | Leu | Thr | Cys | Gln | Ala | Glu | Gly | Tyr |
| 145 | | | | | 150 | | | | | 155 | | | | | 160 |
| Pro | Lys | Ala | Glu | Val | Ile | Trp | Thr | Ser | Ser | Asp | His | Gln | Val | Leu | Ser |
| | | | | 165 | | | | | 170 | | | | | 175 | |
| Gly | Lys | Thr | Thr | Thr | Thr | Asn | Ser | Lys | Arg | Glu | Glu | Lys | Leu | Phe | Asn |
| | | | 180 | | | | | 185 | | | | | 190 | | |
| Val | Thr | Ser | Thr | Leu | Arg | Ile | Asn | Thr | Thr | Thr | Asn | Glu | Ile | Phe | Tyr |
| | | | 195 | | | | | 200 | | | | | 205 | | |
| Cys | Thr | Phe | Arg | Arg | Leu | Asp | Pro | Glu | Glu | Asn | His | Thr | Ala | Glu | Leu |
| | | | 210 | | | | | 215 | | | | | 220 | | |
| Val | Ile | Pro | Glu | Leu | Pro | Leu | Ala | His | Pro | Pro | Asn | Glu | Arg | Thr | His |
| 225 | | | | | 230 | | | | | 235 | | | | | 240 |
| Leu | Val | Ile | Leu | Gly | Ala | Ile | Leu | Leu | Cys | Leu | Gly | Val | Ala | Leu | Thr |
| | | | | 245 | | | | | 250 | | | | | 255 | |
| Phe | Ile | Phe | Arg | Leu | Arg | Lys | Gly | Arg | Met | Met | Asp | Val | Lys | Lys | Cys |
| | | | 260 | | | | | 265 | | | | | 270 | | |
| Gly | Ile | Gln | Asp | Thr | Asn | Ser | Lys | Lys | Gln | Ser | Asp | Thr | His | Leu | Glu |
| | | | 275 | | | | | 280 | | | | | 285 | | |
| Glu | Thr | | | | | | | | | | | | | | |
| | 290 | | | | | | | | | | | | | | |

<210> SEQ ID NO 2
<211> LENGTH: 873
<212> TYPE: DNA
<213> ORGANISM: Homo sapiens

<400> SEQUENCE: 2
atgaggatat tgctgtctt tatattcatg acctactggc atttgctgaa cgcatttact      60
gtcacggttc ccaaggacct atatgtggta gagtatggta gcaatatgac aattgaatgc     120

```
aaattcccag tagaaaaaca attagacctg gctgcactaa ttgtctattg ggaaatggag      180
gataagaaca ttattcaatt tgtgcatgga gaggaagacc tgaaggttca gcatagtagc      240
tacagacaga gggcccggct gttgaaggac cagctctccc tgggaaatgc tgcacttcag      300
atcacagatg tgaaattgca ggatgcaggg gtgtaccgct gcatgatcag ctatggtggt      360
gccgactaca agcgaattac tgtgaaagtc aatgccccat acaacaaaat caaccaaaga      420
attttggttg tggatccagt cacctctgaa catgaactga catgtcaggc tgagggctac      480
cccaaggccg aagtcatctg acaagcagt gaccatcaag tcctgagtgg taagaccacc      540
accaccaatt ccaagagaga ggagaagctt tcaatgtga ccagcacact gagaatcaac      600
acaacaacta atgagatttt ctactgcact tttaggagat tagatcctga ggaaaaccat      660
acagctgaat tggtcatccc agaactacct ctggcacatc ctccaaatga aggactcac       720 ttggtaattc tgggagccat cttattatgc cttggtgtag cactgacatt catcttccgt      780
ttaagaaaag ggagaatgat ggatgtgaaa aatgtggca tccaagatac aaactcaaag       840
aagcaaagtg atacacattt ggaggagacg taa                                    873

<210> SEQ ID NO 3
<211> LENGTH: 873
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgagaatct tcgcggtgtt catcttcatg acctactggc acctcctgaa cgctttcact      60
gtgaccgtgc ctaaggacct ctacgtcgtg aatacggct ccaacatgac catcgagtgc       120
aaattcccag tggagaagca gctggacctg gctgccctga tcgtgtactg ggaaatggag      180
gacaagaaca tcatccaatt cgtgcatggg gaggaggacc tgaaggtcca gcattcgtca      240
tatcggcaaa gagccaggct gctgaaggat cagctgtccc tcggcaatgc ggcactgcag      300
attaccgatg tgaagctgca ggacgccgga gtctaccggt gcatgatttc ctacggcgga      360
gcagactaca agcgcattac cgtgaaggtc aacgctccct acaacaagat caaccagcgg      420
attctggtgg tcgaccctgt gacctccgag catgagctga cctgtcaagc cgaaggttac      480
ccgaaagcgg aagtgatctg acgtcgagc gaccaccagg tcttgagcgg aaagacgacc       540
actactaaca gcaagcggga agagaaactg tttaacgtga ccagcactct tcggatcaac      600
accaccacta cgagattttt ctactgtacc tttcgccggc ttgaccogga gaaaatcac       660 accgccgagc tcgtgatccc cgagctgccc ctcgcccacc ctcctaacga agaacccac       720 ctggtcatct gggggccat cctgctgtgc ctggagtgg ccctgaccttt cattttagg        780 ctccgaaagg gccgcatgat ggacgtgaag aaatgcggaa tccaggacac taactccaag     840
aagcagtccg atactcacct ggaagaaacc tag                                    873

<210> SEQ ID NO 4
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgagaatct tcgcggtgtt catcttcatg acctactggc acctcctgaa cgctttcact      60
```

-continued

```
gtgaccgtgc ctaaggacct ctacgtcgtg gaatacggct ccaacatgac catcgagtgc      120
aaattcccag tggagaagca gctggacctg gctgccctga tcgtgtactg ggaaatggag      180
gacaagaaca tcatccaatt cgtgcatggg gaggaggacc tgaaggtcca gcattcgtca      240
tatcggcaaa gagccaggct gctgaaggat cagctgtccc tcggcaatgc ggcactgcag      300
attaccgatg tgaagctgca ggacgccgga gtctaccggt gcatgatttc ctacggcgga      360
gcagactaca agcgcattac cgtgaaggtc aacgctccct acaacaagat caaccagcgg      420
attctggtgg tcgaccctgt gacctccgag catgagctga cctgtcaagc cgaaggttac      480
ccgaaagcgg aagtgatctg gacgtcgagc gaccaccagg tcttgagcgg aaagacgacc      540
actactaaca gcaagcggga agagaaactg tttaacgtga ccagcactct tcggatcaac      600
accaccacta cgagattttt ctactgtacc tttcgccggc ttgacccgga agaaaatcac      660
accgccgagc tcgtgatccc cgagctgccc ctcgcccacc ctcctaacga agaactccc       720 aagtcttgcg ataagaccca cacatgcccc ccatgcccag ccccgcccgt ggcgggcccc      780
tccgtgtttc ttttcccgcc gaagcctaag gatacccctga tgatctcccg caccccgaa      840 gtcacttgtg tggtggtgga cgtcagccac gaagatccgg aagtcaagtt caattggtac      900
gtggacgggg tcgaagtgca caacgccaag accaagcccc gcgaggaaca gtacaactca      960
acgtaccggg tggtgtccgt gctgaccgtg ctgcatcagg actggctgaa cggaaaggag     1020
tacaagtgca aagtgtccaa caagggactg ccgagctcga tcgaaaagac catttcgaag     1080
gccaaggggc agcctaggga gccacaggtc tataccctcc cgccctcacg agatgaactg     1140
accaagaacc aagtgtcatt gacttgcctc gtgaagggct tctacccttc cgacatcgcc     1200
gtggaatggg aatccaacgg acagccggag aacaactaca agactactcc gcccgtgctt     1260
gactccgacg gttcgttctt cctgtactcc aagctgaccg tggataagtc ccgctggcaa     1320
cagggcaacg tgttctcctg ctccgtgatg cacgaagccc tgcacaacca ctacacccag     1380
aagtccctct cgttgagccc tggaaaatag                                       1410
```

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser
1               5

<210> SEQ ID NO 6
<211> LENGTH: 3832
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ggatctaggt gaagatcctt tttgataatc tcatgaccaa aatcccttaa cgtgagtttt      60
cgttccactg agcgtcagac cccgtagaaa agatcaaagg atcttcttga tccttttt      120 ttctgcgcgt aatctgctgc ttgcaaacaa aaaaaccacc gctaccagcg gtggtttgtt      180
tgccggatca gagctaccaa ctctttttcc gaaggtaac tggcttcagc agagcgcaga     240
```

```
taccaaatac tgtccttcta gtgtagccgt agttaggcca ccacttcaag aactctgtag      300
caccgcctac atacctcgct ctgctaatcc tgttaccagt ggctgctgcc agtggcgata      360
agtcgtgtct taccggggttg gactcaagac gatagttacc ggataaggcg cagcggtcgg     420
gctgaacggg gggttcgtgc acacagccca gcttggagcg aacgacctac accgaactga      480 gataccctaca gcgtgagcta tgagaaagcg ccacgcttcc cgaagggaga aaggcggaca    540
ggtatccggt aagcggcagg gtcggaacag gagagcgcac gagggagctt ccaggggggaa    600 acgcctggta tctttatagt cctgtcgggt ttcgccacct ctgacttgag cgtcgatttt     660
tgtgatgctc gtcagggggg cggagcctat ggaaaaacgc cagcaacgcg ccttttttac     720
ggttcctggg cttttgctgg ccttttgctc acatgttctt gactcttcgc gatgtacggg     780
ccagatatac gcgttgacat tgattattga ctagttatta atagtaatca attacggggt     840
cattagttca tagcccatat atggagttcc gcgttacata acttacggta aatggcccgc     900
ctggctgacc gcccaacgac ccccgcccat tgacgtcaat aatgacgtat gttcccatag     960
taacgccaat agggactttc cattgacgtc aatgggtgga ctatttacgg taaactgccc    1020
acttggcagt acatcaagtg tatcatatgc caagtacgcc ccctattgac gtcaatgacg    1080
gtaaatggcc cgcctggcat tatgcccagt acatgacctt atgggacttt cctacttggc    1140
agtacatcta cgtattagtc atcgctatta ccatggtgat gcggttttgg cagtacatca    1200
atgggcgtgg atagcggttt gactcacggg gatttccaag tctccacccc attgacgtca    1260
atgggagttt gttttggcac caaaatcaac gggactttcc aaaatgtcgt aacaactccg    1320
ccccattgac gcaaatgggc ggtaggcgtg tacggtggga ggtctatata agcagagctc    1380
tctggctaac tagagaaccc actgcttact ggcttatcga aattaatacg actcactata    1440
gggagaccca agctggctag cgtttaaact taagcttcca ccatgagaat cttcgcggtg    1500
ttcatcttca tgacctactg gcacctcctg aacgctttca ctgtgaccgt gcctaaggac    1560
ctctacgtcg tggaatacgg ctccaacatg accatcgagt gcaaattccc agtggagaag    1620
cagctggacc tggctgccct gatcgtgtac tgggaaatgg aggacaagaa catcatccaa    1680
ttcgtgcatg gggaggagga cctgaaggtc cagcattcgt catatcggca aagagccagg    1740
ctgctgaagg atcagctgtc cctcggcaat gcggcactgc agattaccga tgtgaagctg    1800
caggacgccg gagtctaccg gtgcatgatt tcctacggcg gagcagacta caagcgcatt    1860
accgtgaagg tcaacgctcc ctacaacaag atcaaccagc ggattctggt ggtcgaccct    1920
gtgacctccg agcatgagct gacctgtcaa gccgaaggtt acccgaaagc ggaagtgatc    1980
tggacgtcga gcgaccacca ggtcttgagc ggaaagacga ccactactaa cagcaagcgg    2040
gaagagaaac tgtttaacgt gaccagcact cttcggatca acaccaccac taacgagatt    2100
ttctactgta cctttcgccg gcttgacccg gaagaaaatc acaccgccga gctcgtgatc    2160
cccgagctgc ccctcgccca ccctcctaac gaaagaaccc acctggtcat cttgggggcc    2220
atcctgctgt gcctgggagt ggccctgacc ttcatttttta ggctccgaaa gggccgcatg    2280
atggacgtga agaaatgcgg aatccaggac actaactcca agaagcagtc cgatactcac    2340
ctggaagaaa cctaggaatt ccagcacagt ggcggccgct cgagtctaga gggcccgttt    2400
aaacccgctg atcagcctcg actgtgcctt ctagttgcca gccatctgtt gtttgcccct    2460
cccccgtgcc ttccttgacc ctggaaggtg ccactcccac tgtcctttcc taataaaatg    2520
aggaaattgc atcgcattgt ctgagtaggt gtcattctat tctggggggt ggggtggggc    2580
```

| | | | | |
|---|---|---|---|---|
| aggacagcaa | gggggaggat | tgggaagaca | atagcaggca | tgctggggat gcggtgggct | 2640 |
| ctatggcttc | tactgggcgg | ttttatggac | agcaagcgaa | ccggaattgc cagctggggc | 2700 |
| gccctctggt | aaggttggga | agccctgcaa | agtaaactgg | atggctttct cgccgccaag | 2760 |
| gatctgatgg | cgcaggggat | caagctctga | tcaagagaca | ggatgaggat cgtttcgcat | 2820 |
| gattgaacaa | gatggattgc | acgcaggttc | tccggccgct | tgggtggaga ggctattcgg | 2880 |
| ctatgactgg | gcacaacaga | caatcggctg | ctctgatgcc | gccgtgttcc ggctgtcagc | 2940 |
| gcagggggcgc | ccggttcttt | ttgtcaagac | cgacctgtcc | ggtgccctga atgaactgca | 3000 |
| agacgaggca | gcgcggctat | cgtggctggc | cacgacgggc | gttccttgcg cagctgtgct | 3060 |
| cgacgttgtc | actgaagcgg | gaagggactg | gctgctattg | ggcgaagtgc cggggcagga | 3120 |
| tctcctgtca | tctcaccttg | ctcctgccga | gaaagtatcc | atcatggctg atgcaatgcg | 3180 |
| gcggctgcat | acgcttgatc | cggctacctg | cccattcgac | caccaagcga acatcgcat | 3240 |
| cgagcgagca | cgtactcgga | tggaagccgg | tcttgtcgat | caggatgatc tggacgaaga | 3300 |
| gcatcagggg | ctcgcgccag | ccgaactgtt | cgccaggctc | aaggcgagca tgcccgacgg | 3360 |
| cgaggatctc | gtcgtgaccc | atggcgatgc | ctgcttgccg | aatatcatgg tggaaaatgg | 3420 |
| ccgcttttct | ggattcatcg | actgtggccg | gctgggtgtg | gcggaccgct atcaggacat | 3480 |
| agcgttggct | acccgtgata | ttgctgaaga | gcttggcggc | gaatgggctg accgcttcct | 3540 |
| cgtgctttac | ggtatcgccg | ctcccgattc | gcagcgcatc | gccttctatc gccttcttga | 3600 |
| cgagttcttc | tgaattatta | acgcttacaa | tttcctgatg | cggtattttc tccttacgca | 3660 |
| tctgtgcggt | atttcacacc | gcatacaggt | ggcactttc | ggggaaatgt gcgcggaacc | 3720 |
| cctatttgtt | tattttcta | aatacattca | aatatgtatc | cgctcatgag acaataaccc | 3780 |
| tgataaatgc | ttcaataata | gcacgtgcta | aaacttcatt | tttaatttaa aa | 3832 |

<210> SEQ ID NO 7
<211> LENGTH: 4369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | | | | |
|---|---|---|---|---|
| ggatctaggt | gaagatcctt | tttgataatc | tcatgaccaa | aatcccttaa cgtgagtttt | 60 |
| cgttccactg | agcgtcagac | cccgtagaaa | agatcaaagg | atcttcttga tccttttt | 120 |
| ttctgcgcgt | aatctgctgc | ttgcaaacaa | aaaaaccacc | gctaccagcg gtggtttgtt | 180 |
| tgccggatca | agagctacca | actctttttc | cgaaggtaac | tggcttcagc agagcgcaga | 240 |
| taccaaatac | tgtccttcta | gtgtagccgt | agttaggcca | ccacttcaag aactctgtag | 300 |
| caccgcctac | atacctcgct | ctgctaatcc | tgttaccagt | ggctgctgcc agtggcgata | 360 |
| agtcgtgtct | taccgggttg | gactcaagac | gatagttacc | ggataaggcg cagcggtcgg | 420 |
| gctgaacggg | gggttcgtgc | acacagccca | gcttggagcg | aacgacctac accgaactga | 480 |
| gatacctaca | gcgtgagcta | tgagaaagcg | ccacgcttcc | cgaagggaga aaggcggaca | 540 |
| ggtatccggt | aagcggcagg | gtcggaacag | gagagcgcac | gagggagctt ccaggggaa | 600 |
| acgcctggta | tctttatagt | cctgtcgggt | ttcgccacct | ctgacttgag cgtcgatttt | 660 |
| tgtgatgctc | gtcagggggg | cggagcctat | ggaaaaacgc | cagcaacgcg gccttttac | 720 |
| ggttcctggg | cttttgctgg | cctttgctc | acatgttctt | gactcttcgc gatgtacggg | 780 |

```
ccagatatac gcgttgacat tgattattga ctagttatta atagtaatca attacggggt    840
cattagttca tagcccatat atggagttcc gcgttacata acttacggta aatggcccgc    900
ctggctgacc gcccaacgac ccccgcccat tgacgtcaat aatgacgtat gttcccatag    960
taacgccaat agggactttc cattgacgtc aatgggtgga ctatttacgg taaactgccc   1020
acttggcagt acatcaagtg tatcatatgc caagtacgcc ccctattgac gtcaatgacg   1080
gtaaatggcc cgcctggcat tatgcccagt acatgacctt atgggacttt cctacttggc   1140
agtacatcta cgtattagtc atcgctatta ccatggtgat gcggttttgg cagtacatca   1200
atgggcgtgg atagcggttt gactcacggg gatttccaag tctccacccc attgacgtca   1260
atgggagttt gttttggcac caaaatcaac gggactttcc aaaatgtcgt aacaactccg   1320
ccccattgac gcaaatgggc ggtaggcgtg tacggtggga ggtctatata agcagagctc   1380
tctggctaac tagagaaccc actgcttact ggcttatcga aattaatacg actcactata   1440
gggagaccca gctggctag cgtttaaact taagcttcca ccatgagaat cttcgcggtg   1500
ttcatcttca tgacctactg gcacctcctg aacgctttca ctgtgaccgt gcctaaggac   1560
ctctacgtcg tggaatacgg ctccaacatg accatcgagt gcaaattccc agtgagaag   1620 cagctggacc tggctgccct gatcgtgtac tgggaaatgg aggacaagaa catcatccaa   1680
ttcgtgcatg gggaggagga cctgaaggtc cagcattcgt catatcggca aagagccagg   1740
ctgctgaagg atcagctgtc cctcggcaat gcggcactgc agattaccga tgtgaagctg   1800
caggacgccg gagtctaccg gtgcatgatt tcctacggcg gagcagacta caagcgcatt   1860
accgtgaagg tcaacgctcc ctacaacaag atcaaccagc ggattctggt ggtcgaccct   1920
gtgacctccg agcatgagct gacctgtcaa gccgaaggtt acccgaaagc ggaagtgatc   1980
tggacgtcga gcgaccacca ggtcttgagc ggaaagacga ccactactaa cagcaagcgg   2040
gaagagaaac tgtttaacgt gaccagcact cttcggatca acaccaccac taacgagatt   2100
ttctactgta cctttcgccg gcttgacccg gaagaaaatc acaccgccga gctcgtgatc   2160
cccgagctgc ccctcgccca ccctcctaac gaaagaactc ccaagtcttg cgataagacc   2220
cacacatgcc cgccatgccc agcccgcccc gtggcgggcc cctccgtgtt tctttttcccg   2280 ccgaagccta aggataccct gatgatctcc cgcacccccg aagtcacttg tgtggtggtg   2340
gacgtcagcc acgaagatcc ggaagtcaag ttcaattggt acgtggacgg ggtcgaagtg   2400
cacaacgcca agaccaagcc ccgcgaggaa cagtacaact caacgtaccg ggtggtgtcc   2460
gtgctgaccg tgctgcatca ggactggctg aacggaaagg agtacaagtg caaagtgtcc   2520
aacaagggac tgccgagctc gatcgaaaag accatttcga aggccaaggg gcagcctagg   2580
gagccacagg tctatacct cccgcccctca cgagatgaac tgaccaagaa ccaagtgtca   2640
ttgacttgcc tcgtgaaggg cttctaccct tccgacatcg ccgtggaatg ggaatccaac   2700
ggacagccgg agaacaacta caagactact ccgcccgtgc ttgactccga cggttcgttc   2760
ttcctgtact ccaagctgac cgtggataag tcccgctggc aacagggcaa cgtgttctcc   2820
tgctccgtga tgcacgaagc cctgcacaac cactacaccc agaagtccct ctcgttgagc   2880
cctggaaaat aggaattcca gcacagtggc ggccgctcga gtctagaggg cccgtttaaa   2940
cccgctgatc agcctcgact gtgccttcta gttgccagcc atctgttgtt tgcccctccc   3000
ccgtgccttc cttgaccctg gaaggtgcca ctcccactgt cctttcctaa taaaatgagg   3060
aaattgcatc gcattgtctg agtaggtgtc attctattct ggggggtggg gtggggcagg   3120
acagcaaggg ggaggattgg gaagacaata gcaggcatgc tggggatgcg gtgggctcta   3180
```

```
tggcttctac tgggcggttt tatggacagc aagcgaaccg gaattgccag ctggggcgcc    3240
ctctggtaag gttgggaagc cctgcaaagt aaactggatg gctttctcgc cgccaaggat    3300
ctgatggcgc aggggatcaa gctctgatca agagacagga tgaggatcgt ttcgcatgat    3360
tgaacaagat ggattgcacg caggttctcc ggccgcttgg gtggagaggc tattcggcta    3420
tgactgggca caacagacaa tcggctgctc tgatgccgcc gtgttccggc tgtcagcgca    3480
ggggcgcccg gttcttttg tcaagaccga cctgtccggt gccctgaatg aactgcaaga    3540
cgaggcagcg cggctatcgt ggctggccac gacgggcgtt ccttgcgcag ctgtgctcga    3600
cgttgtcact gaagcgggaa gggactggct gctattgggc gaagtgccgg ggcaggatct    3660
cctgtcatct caccttgctc ctgccgagaa agtatccatc atggctgatg caatgcggcg    3720
gctgcatacg cttgatccgg ctacctgccc attcgaccac caagcgaaac atcgcatcga    3780
gcgagcacgt actcggatgg aagccggtct tgtcgatcag gatgatctgg acgaagagca    3840 tcagggctc gcgccagccg aactgttcgc caggctcaag gcgagcatgc ccgacggcga    3900
ggatctcgtc gtgacccatg gcgatgcctg cttgccgaat atcatggtgg aaaatggccg    3960
cttttctgga ttcatcgact gtggccggct gggtgtggcg gaccgctatc aggacatagc    4020
gttggctacc cgtgatattg ctgaagagct tggcggcgaa tgggctgacc gcttcctcgt    4080
gctttacggt atcgccgctc ccgattcgca gcgcatcgcc ttctatcgcc ttcttgacga    4140
gttcttctga attattaacg cttacaattt cctgatgcgg tattttctcc ttacgcatct    4200
gtgcggtatt tcacaccgca tacaggtggc acttttcggg gaaatgtgcg cggaacccct    4260
atttgtttat ttttctaaat acattcaaat atgtatccgc tcatgagaca ataaccctga    4320
taaatgcttc aataatagca cgtgctaaaa cttcattttt aatttaaaa                4369
```

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Gly Gly Gly Gly Ser Gly Gly Gly Gly Ser Gly Gly Gly Gly Ser
1               5                   10                  15

INTESTINAL EXPRESSION OF PROGRAMMED DEATH LIGAND 1

FIELD OF THE INVENTION

The present disclosure relates to methods and compositions for the amelioration of inflammatory disorders employing gene expression of PD-L1.

BACKGROUND OF THE INVENTION

Immune activation in general, and the T cell activation state in particular, are subject to complex overlapping regulatory mechanisms mediated by a host of costimulatory (e.g. CD28, ICOS, OX40, etc.) and co-inhibitory (e.g., CTLA-4, programmed death-1 ("PD-1"), etc.) molecules on T cells. Programmed death ligand-1 ("PD-L1", also known as B7H1) is constitutively expressed by dendritic cells and other antigen presenting cells and via its interaction with PD-1 appears to mediate T cell down-regulation. Patsoukis et al., Selective effects of PD-1 on Akt and Ras pathways regulate molecular components of the cell cycle and inhibit T cell proliferation, *Sci. Signal* 5: ra46 (2012).

Unfortunately, however, the effect of PD-L1 interaction with CD80 is less clear, as is the interaction between these two pathways. In some settings, blockade of PD-1 by way of soluble PD-L1 can potently enhance the T cell response, and enhance graft-versus-host disease ("GvHD"). Blazar et al., Blockade of Programmed Death-1 Engagement Accelerates Graft-Versus-Host Lethality by an IFN-γ-Dependent Mechanism *J. Immunol.* 171:1272-77 (2003). Conversely, other researchers were able to ameliorate GvHD with a soluble form of PD-L1 but only in a PD-L1 knock-out background. Deng et al. B7H1/CD80 Interaction Augments PD-1 Dependent T Cell Apoptosis and Ameliorates Graft-versus-Host Disease, *J. Immunol.* 194:560-74 (2105). Moreover, it appears that role of peripheral dendritic cells on the T cell response is more complicated than once thought. For example, while immature peripheral dendritic cells normally do not initiate T cell differentiation, populations of dendritic cells have been observed infiltrating the central nervous system (CNS) and facilitating epitope spreading in experimental autoimmune encephalomyelitis (EAE) mouse models. Spagnuolo et al., Involvement of Immune Regulation in Multiple Sclerosis, *Immunology and Immunogenetics Insights* 9:1-10.

Accordingly, there is a clear need in the art to better understand the role of PD-L1 in T cell activation in immune protective settings, to better exploit the therapeutic potential of PD-L1 in inflammatory disorders.

SUMMARY OF THE INVENTION

The present invention resolves the foregoing scientific uncertainties in the prior art by successfully employing localized intestinal expression of PD-L1 polypeptides, including soluble PD-L1 polypeptides, in an immune protective setting for the treatment of a variety of inflammatory disorders including, e.g., inflammatory bowel disease (e.g. ulcerative colitis, Crohn's disease, and the like) as well as graft-versus-host disease (GvHD) induced by organ or bone marrow transplant. In one aspect, therefore, the invention provides a method of treating an inflammatory disorder in a patient in need thereof, comprising administering to the intestinal tract of said patient an expression vector comprising a PD-L1 nucleic acid.

In one embodiment, the PD-L1 polypeptide is a membrane-bound PD-L1 polypeptide. In preferred embodiments, the PD-L1 polypeptide is human PD-L1 or splice variants thereof. In one such embodiment, the PD-L1 nucleic acid encodes for a PD-L1 polypeptide comprising the amino acid sequence of SEQ ID NO: 1 or an amino acid sequence that is at least about 80%, 85%, 90%, 95%, 96%, 97%, 98% or 99% identical to SEQ ID NO: 1.

In alternative embodiments, the PD-L1 polypeptide is a soluble PD-L1 polypeptide, e.g. comprises the signal sequence, IgV domain and IgC domain of PD-L1, and preferably human PD-L1 (i.e. amino acids 1-239 of SEQ ID NO: 1). In some embodiments, the soluble PD-L1 polypeptide may lack all or part of the signal sequence (e.g. it may comprise amino acids 19-238 of SEQ ID NO: 1).

In some embodiments, the PD-L1 nucleic acid is delivered by an expression vector encapsulated in a nucleic acid delivery vehicle. Preferred nucleic acid delivery vehicles include chitosan or chitosan derivative nanoparticles. In one such embodiment, the chitosan derivative nanoparticles comprise chitosan coupled with arginine and/or gluconic acid. In another such embodiment, the chitosan derivative nanoparticles comprise chitosan coupled with arginine and a hydrophilic polyol. In one embodiment, the hydrophilic polyol is glucose.

In another aspect, the invention provides expression vectors comprising a PD-L1 nucleic acid to treat an inflammatory disorder in a patient in need thereof, wherein said expression vector is administered to the intestine of said subject. In some embodiments, the PD-L1 nucleic acid comprises SEQ ID NO: 2. Preferably, the PD-L1 nucleic acid comprises at least one synonymous mutation in SEQ ID NO: 2. Still more preferably, the PD-L1 nucleic acid comprises a plurality of such mutations to assist in differentiation and, optionally, improved expression. In an exemplary embodiment, the PD-L1 nucleic acid comprises SEQ ID NO: 3.

In some embodiments, the PD-L1 nucleic acid further comprises a heterologous sequence. The heterologous sequence may comprise an Fc domain, a protein tag, a conjugated therapeutic, or a combination thereof. In one embodiment, the N-terminal region of the PD-L1 polypeptide is fused to a human IgG1 Fc region or portion thereof. The PD-L1 polypeptide may be fused to a human IgG1 Fc region or portion thereof by way of an amino acid sequence of (GGGGS)n (SEQ ID NO: 5). In some embodiments, the IgG1 Fc is mutated to reduce antibody-dependent cellular cytotoxicity (ADCC) and complement-dependent cellular cytotoxicity (CDCC) by altering one or more of the following amino acids in the Fc domain: E233P, L234V, L235A, deletion of G236, A327G, A330S and P331S. In an exemplary embodiment, the PD-L1 nucleic acid comprises SEQ ID NO: 4.

Inflammatory disorders that can be advantageously treated by way of the subject invention include both chronic and acute conditions, including inflammation associated with infection (e.g. septic shock, sepsis, or systemic inflammatory response syndrome (SIRS)), ischemia-reperfusion injury, endotoxin lethality, inflammatory bowel disease, Crohn's disease, colitis, or resulting from over production of cytokines (e.g. TNF or IL-1) as well as GvHD.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The present disclosure is disclosed with reference to the accompanying drawings, wherein:

FIG. 1: The pVax-hPD-L1 vector (SEQ ID NO: 6). Plasmid sequence of the vector encoding a membrane-bound human PD-L1 polypeptide, the optimized human PD-L1 cDNA is highlighted.

FIG. 2: The pVax-hPD-L1 Fc vector (SEQ ID NO: 7). Plasmid sequence of the vector encoding a soluble human PD-L1 Fc polypeptide, the optimized human PD-L1 cDNA is highlighted.

FIG. 7: Plasmid DNA-generated PD-L1-Fc suppresses T cell activation in vitro. (A) Purified CD4+ T cells were isolated from three C57BL/6 mice and pooled. Cells were seeded into a 96-well flat-bottomed plate that was pre-coated with anti-CD3 (0.2 μg/ml) alone or with 5 μg/ml serum free media produced PD-L1-Fc. Recombinant IgG1-Fc and recombinant PD-L1-Fc were used as controls. Cells were stimulated for 3 days, and cell activation was measured by detecting cell size in the FSC-SSC gate by flow cytometry. (B) NIH/3T3 cells were transfected with wild-type PD-L1 plasmid DNA or control (pVax;) in a 6-well plate. Forty-eight hours post-transfection, cells were re-seeded in a 96-well v-bottom plate, and incubated with recombinant human PD-1 at various concentrations. Cells were washed and stained with APC-conjugated anti-human PD-1 or isotype control, and PD-1 binding was analyzed by flow cytometry by assessing APC detection on transfected cells. The binding of PE-conjugated anti-human PD-L1 or isotype control was also assessed. A reduction in the binding of anti-human PD-L1-PE is predicted to be the result of steric hindrance of antibody binding given that the recombinant PD-1 has bound to the PD-L1 expressed on the NIH/3T3 cells.

DETAILED DESCRIPTION

Figure 3A:
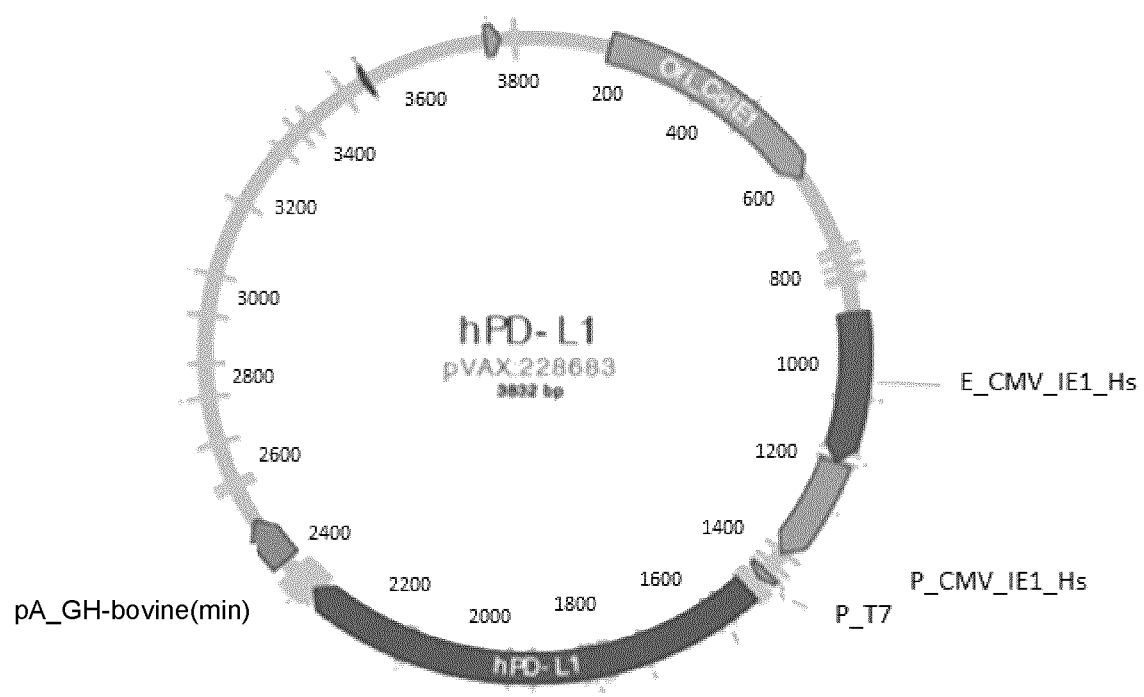
FIG. 3A: Human PD-L1 plasmid and in vitro expression. (A) Plasmid map of the optimized hPD-L1 DNA sequences cloned in a pVax backbone containing a plasmid replication origin (pUC ori;) under the control of a human cytomegalovirus immediate-early gene promoter (CMV;) with a kanamycin resistance gene.
Figure 3B:
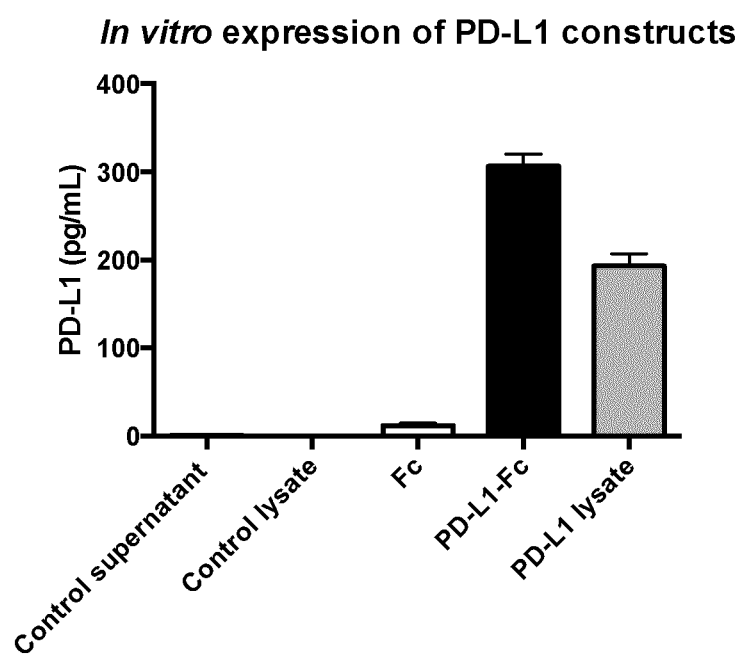
FIG. 3B: In vitro PD-L1 and PD-L1-Fc expression: HEK293T cells were transfected with 1 μg or 2.5 μg of Fc control (White), PD-L1-Fc (Black), or PD-L1 (Grey) plasmid DNA using Lipofectamine 2000 (Invitrogen). PD-L1 protein content in cell culture supernatant or cell lysate was quantified 48 h post-transfection.

The present invention contemplates the intestinal expression of PD-L1 nucleic acids for the treatment of inflammatory disorders.

PD-L1 Proteins and Polynucleotides

The PD-L1 polypeptides contemplated herein include the full-length sequence, soluble fragments, and variants thereof.

Full-length PD-L1 proteins generally comprise a signal sequence, an IgV domain, and an IgC domain, a transmembrane domain, and a cytoplasmic domain. The human sequences are available to the public at the GenBank database under NM_014143.3 and NP_054862.1. The sequence of human PD-L1 transcript variant 1 is the canonical sequence, and all positional information described with respect to known isoforms are determined from this sequence. In this isoform, the signal sequence is shown from about amino acid 1 to about amino acid 18, the IgV domain is shown from about amino acid 19 to about amino acid 134, the IgC domain is shown from about amino acid 135 to about amino acid 227, the transmembrane domain is shown from about amino acid 239 to about amino acid 259, and the cytoplasmic domain is shown from about amino acid 260 to about amino acid 290. At least five transcript (i.e., splice) variants encoding different human PD-L1 isoforms are known and are described, e.g. in U.S. Patent Publication No. 2016/0122829, the disclosure of which is expressly incorporated by reference herein.

Nucleic acid and amino acid sequence information for PD-L1 in multiple species is well known in the art and readily available in public databases, including, for example, monkey PD-L1 (NM 001083889.1 and NP_001077358.1), chimpanzee PD-L1 (XM_0011401705.2 and XP_001140705.1), mouse PD-L1 (NM 021893.3 and NP_068693.1), rat PD-L1 (NM_001191954.1 and NP_001178883.1), chicken PD-L1 (XM_424811.3 and XP_424811.3), cow PD-L1 (NM_001163412.1 and NP_001156884.1), and dog PD-L1 (XM_541302.3 and XP_541302.3).

The PD-L1 nucleic acids of the subject invention will generally comprise a nucleic acid sequence encoding a human PD-L1 polypeptide, wherein the PD-L1 polypeptide preferably comprises an amino acid sequence of SEQ ID NO: 1 or an amino acid sequence that is at least about 80%, 85%, 90%, 95%, 96%, 97%, 98% or 99% identical to SEQ ID NO: 1, or fragments thereof. In some embodiments, the PD-L1 polypeptide is membrane-bound, i.e. full-length PD-L1 including the transmembrane and cytoplasmic domains. In alternative embodiments, the PD-L1 polypeptide is a soluble PD-L1 polypeptide comprising at least the IgV domain and IgC domains of human PD-L1, and optionally further comprising the signal sequence. In one embodiment, the PD-L1 polypeptide comprises amino acids 1-239 of SEQ ID NO: 1, which corresponds to nucleotides 1-717 of the full-length cDNA sequence. In other embodiments, the soluble PD-L1 polypeptide may lack all or part of the signal sequence (e.g. it may comprise amino acids 19-239 of SEQ ID NO: 1). See, e.g., U.S. Patent Publication No. 2017/0189476, the disclosure of which is expressly incorporated by reference herein.

TABLE 1

Amino Acid sequence for human PD-L1

MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET (SEQ ID

NO: 1)

In some embodiments, PD-L1 nucleic acid is identical to the native PD-L1 nucleic acid sequence (SEQ ID NO: 2) or a fragment thereof. Preferably, at least one synonymous nucleic acid substitution is made to allow differentiation and detection of the resulting transcript from endogenous human PD-L1 nucleotide following administration of the subject nucleic acids, and still more preferably a plurality of such synonymous mutations are made. In particularly preferred embodiments, the PD-L1 nucleic acid sequence is codon-optimized to improve expression. In an exemplary embodiment, the PD-L1 nucleic acid preferably comprises the nucleic acid sequence of SEQ ID NO: 3 or a sequence that is at least about 70%, 80%, 85%, 90%, 95%, 96%, 97%, 98% or 99% identical to SEQ ID NO: 3.

In some embodiments, the PD-L1 polypeptides of the subject invention may be fused to an Fc region or portion thereof. In an exemplary embodiment, the PD-L1 nucleic acid comprises the nucleic sequence of SEQ ID NO: 4 or a nucleic acid sequence that is at least about 70%, 80%, 85%, 90%, 95%, 96%, 97%, 98% or 99% identical to SEQ ID NO: 4.

The PD-L1 nucleic acids of the subject invention may include exons 1-4 in their entirety, as well as the first 35 nucleotides of exon 5. It is noted that the ATG site (start codon) is found at position 13 in exon 2. Therefore, the PD-L1 nucleic acids of the subject invention may include the last 52 nucleotides of exon 2, all of exon 3 and 4, as well as the first 35 nucleotides of exon 5.

TABLE 2

Nucleic Acid Sequence for human PD-L1

ATGAGGATATTTGCTGTCTTTATATTCATGACCTACTGGCATTTGCTGAA

CGCATTTACTGTCACGGTTCCCAAGGACCTATATGTGGTAGAGTATGGTA

GCAATATGACAATTGAATGCAAATTCCCAGTAGAAAAACAATTAGACCTG

TABLE 2-continued

Nucleic Acid Sequence for human PD-L1

GCTGCACTAATTGTCTATTGGGAAATGGAGGATAAGAACATTATTCAATT

TGTGCATGGAGAGGAAGACCTGAAGGTTCAGCATAGTAGCTACAGACAGA

GGGCCCGGCTGTTGAAGGACCAGCTCTCCCTGGGAAATGCTGCACTTCAG

ATCACAGATGTGAAATTGCAGGATGCAGGGGTGTACCGCTGCATGATCAG

CTATGGTGGTGCCGACTACAAGCGAATTACTGTGAAAGTCAATGCCCCAT

ACAACAAAATCAACCAAAGAATTTTGGTTGTGGATCCAGTCACCTCTGAA

CATGAACTGACATGTCAGGCTGAGGGCTACCCCAAGGCCGAAGTCATCTG

GACAAGCAGTGACCATCAAGTCCTGAGTGGTAAGACCACCACCACCAATT

CCAAGAGAGAGGAGAAGCTTTTCAATGTGACCAGCACACTGAGAATCAAC

ACAACAACTAATGAGATTTTCTACTGCACTTTTAGGAGATTAGATCCTGA

GGAAAACCATACAGCTGAATTGGTCATCCCAGAACTACCTCTGGCACATC

CTCCAAATGAAAGGACTCACTTGGTAATTCTGGGAGCCATCTTATTATGC

CTTGGTGTAGCACTGACATTCATCTTCCGTTTAAGAAAAGGGAGAATGAT

GGATGTGAAAAAATGTGGCATCCAAGATACAAACTCAAAGAAGCAAAGTG

ATACACATTTGGAGGAGACGTAA (SEQ ID NO. 2)

TABLE 3

Codon Optimized Nucleic Acid Sequence of Membrane-
Bound PD-L1

ATGAGAATCTTCGCGGTGTTCATCTTCATGACCTACTGGCACCTCCTGAA

CGCTTTCACTGTGACCGTGCCTAAGGACCTCTACGTCGTGGAATACGGCT

CCAACATGACCATCGAGTGCAAATTCCCAGTGGAGAAGCAGCTGGACCTG

GCTGCCCTGATCGTGTACTGGGAAATGGAGGACAAGAACATCATCCAATT

CGTGCATGGGGAGGAGGACCTGAAGGTCCAGCATTCGTCATATCGGCAAA

GAGCCAGGCTGCTGAAGGATCAGCTGTCCCTCGGCAATGCGGCACTGCAG

ATTACCGATGTGAAGCTGCAGGACGCCGGAGTCTACCGGTGCATGATTTC

CTACGGCGGAGCAGACTACAAGCGCATTACCGTGAAGGTCAACGCTCCCT

ACAACAAGATCAACCAGCGGATTCTGGTGGTCGACCCTGTGACCTCCGAG

CATGAGCTGACCTGTCAAGCCGAAGGTTACCCGAAAGCGGAAGTGATCTG

GACGTCGAGCGACCACCAGGTCTTGAGCGGAAAGACGACCACTACTAACA

GCAAGCGGGAAGAGAAACTGTTTAACGTGACCAGCACTCTTCGGATCAAC

ACCACCACTAACGAGATTTTCTACTGTACCTTTCGCCGGCTTGACCCGGA

AGAAAATCACACCGCCGAGCTCGTGATCCCCGAGCTGCCCCTCGCCCACC

CTCCTAACGAAAGAACCCACCTGGTCATCTTGGGGGCCATCCTGCTGTGC

CTGGGAGTGGCCCTGACCTTCATTTTTAGGCTCCGAAAGGGCCGCATGAT

GGACGTGAAGAAATGCGGAATCCAGGACACTAACTCCAAGAAGCAGTCCG

ATACTCACCTGGAAGAAACCTAG (SEQ ID NO. 3)

TABLE 4

Codon Optimized Nucleic Acid Sequence of Soluble PD-L1 Fused With an Fc Fragment

ATGAGAATCTTCGCGGTGTTCATCTTCATGACCTACTGGCACCTCCTGAA

CGCTTTCACTGTGACCGTGCCTAAGGACCTCTACGTCGTGGAATACGGCT

CCAACATGACCATCGAGTGCAAATTCCCAGTGGAGAAGCAGCTGGACCTG

GCTGCCCTGATCGTGTACTGGGAAATGGAGGACAAGAACATCATCCAATT

CGTGCATGGGGAGGAGGACCTGAAGGTCCAGCATTCGTCATATCGGCAAA

GAGCCAGGCTGCTGAAGGATCAGCTGTCCCTCGGCAATGCGGCACTGCAG

ATTACCGATGTGAAGCTGCAGGACGCCGGAGTCTACCGGTGCATGATTTC

CTACGGCGGAGCAGACTACAAGCGCATTACCGTGAAGGTCAACGCTCCCT

ACAACAAGATCAACCAGCGGATTCTGGTGGTCGACCCTGTGACCTCCGAG

CATGAGCTGACCTGTCAAGCCGAAGGTTACCCGAAAGCGAAGTGATCTG

GACGTCGAGCGACCACCAGGTCTTGAGCGGAAAGACGACCACTACTAACA

GCAAGCGGGAAGAGAAACTGTTTAACGTGACCAGCACTCTTCGGATCAAC

ACCACCACTAACGAGATTTTCTACTGTACCTTTCGCCGGCTTGACCCGGA

AGAAAATCACACCGCCGAGCTCGTGATCCCCGAGCTGCCCCTCGCCCACC

CTCCTAACGAAAGAACTCCCAAGTCTTGCGATAAGACCCACACATGCCCG

CCATGCCCAGCCCCGCCCGTGGCGGGCCCCTCCGTGTTTCTTTTCCCGCC

GAAGCCTAAGGATACCCTGATGATCTCCCGCACCCCCGAAGTCACTTGTG

TGGTGGTGGACGTCAGCCACGAAGATCCGGAAGTCAAGTTCAATTGGTAC

GTGGACGGGGTCGAAGTGCACAACGCCAAGACCAAGCCCCGCGAGGAACA

GTACAACTCAACGTACCGGTGGTGTCCGTGCTGACCGTGCTGCATCAGG

ACTGGCTGAACGGAAAGGAGTACAAGTGCAAAGTGTCCAACAAGGGACTG

CCGAGCTCGATCGAAAAGACCATTTCGAAGGCCAAGGGGCAGCCTAGGGA

GCCACAGGTCTATACCCTCCCGCCCTCACGAGATGAACTGACCAAGAACC

AAGTGTCATTGACTTGCCTCGTGAAGGGCTTCTACCCTTCCGACATCGCC

GTGGAATGGGAATCCAACGGACAGCCGGAGAACAACTACAAGACTACTCC

GCCCGTGCTTGACTCCGACGGTTCGTTCTTCCTGTACTCCAAGCTGACCG

TGGATAAGTCCCGCTGGCAACAGGGCAACGTGTTCTCCTGCTCCGTGATG

CACGAAGCCCTGCACAACCACTACACCCAGAAGTCCCTCTCGTTGAGCCC

TGGAAAATAG (SEQ ID NO. 4)

There is a known and definite correspondence between the amino acid sequence of a particular protein and the nucleotide sequences that can code for the protein, as defined by the genetic code. Likewise, there is a known and definite correspondence between the nucleotide sequence of a particular nucleic acid and the amino acid sequence encoded by that nucleic acid, as defined by the genetic code.

TABLE 3

| GENETIC CODE | |
|---|---|
| Alanine (Ala, A) | GCA, GCC, GCG, GCT |
| Arginine (Arg, R) | AGA, ACG, CGA, CGC, CGG, CGT |

TABLE 3-continued

| GENETIC CODE | |
|---|---|
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |

An important and well known feature of the genetic code is its redundancy, whereby, for most of the amino acids used to make proteins, more than one coding nucleotide triplet may be employed. Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a polynucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

In some embodiments, the PD-L1 proteins of the present invention do not contain the signal sequence as such a sequence is usually cleaved prior to secretion of the polypeptide from the cell. In other embodiments, the PD-L1 proteins are soluble, i.e. consist of the IgV domain and the IgC domain (i.e., the extracellular portion of the full-length, membrane-bound PD-L1) and can further comprise heterologous sequences, such as Fc domains, protein tags, conjugated therapeutics, and the like. Such soluble PD-L1 isoforms can be generated by alternative splicing in a number of ways well known to the skilled artisan.

In preferred embodiments, the soluble PD-L1 comprises the elimination of part of exon 5 and the entirety of exons 6 and 7 of full-length, membrane-bound PD-L1 cDNA, as illustrated in FIG. 2 herein. The soluble PD-L1 isoforms can be generated by fusing the N terminal region of PD-L1 to human IgG1 Fc and, in some embodiments, can be linked by amino acid sequences (GGGGS)n (SEQ ID NO: 5). In preferred embodiments, the IgG1 Fc can be mutated to reduce antibody-dependent cellular cytotoxicity (ADCC) and complement-dependent cellular cytotoxicity (CDCC) by altering the following amino acids in the Fc domain: E233P, L234V, L235A, deletion of G236, A327G, A330S and P331S. The Fc domain may be of human origin and may also be derived from the Fc of human IgG1.

Nucleic Acid Delivery Vehicles

Administration of an expression vector comprising a PD-L1 nucleic acid so as to achieve effective intestinal expression can be accomplished using any method known in the art. In preferred embodiments, administration of the subject nucleic acid delivery vehicles is localized to the gut (i.e. not systemically administered). In one embodiment, the nucleic acid delivery vehicle comprises a viral vector. In another embodiment, the nucleic acid delivery vehicle comprises a cationic liposome. In preferred embodiments, the nucleic acid delivery vehicle comprises chitosan. In alternative embodiments, biological gene delivery vehicles (BGV) are used such as, e.g., gut bacteria, bacteriophage, virus-like particles, biological liposomes, or the like, to deliver a PD-L1 polynucleotide to gut epithelium. For a review of BGVs currently under investigation, see Seow and Wood, Biological Gene Delivery Vehicles Beyond Viral Vectors, Molecular Therapy 17:767-777 (2009), the contents of which are herein incorporated in their entirety.

In particular embodiments, the nucleic acid delivery vehicle comprises a chitosan derivative, e.g., a chitosan that incorporates an additional functionalization, e.g., with an attached ligand. "Chitosan" as used herein will be understood to include the broad category of chitosan-based polymers comprising covalently modified N-acetyl-D-glucosamine and/or D-glucosamine units, as well as chitosan-based polymers incorporating other units, or attached to other moieties. Derivatives are frequently based on a modification of the hydroxyl group or the amine group of glucosamine, such as done with arginine-functionalized chitosan. Examples of chitosan derivatives include, but are not limited to, trimethylated chitosan, PEGylated chitosan, thiolated chitosan, galactosylated chitosan, alkylated chitosan, PEI-incorporated chitosan, uronic acid modified chitosan, glycol chitosan, and the like. For further teaching on chitosan derivatives, see, for example, pp. 63-74 of "Non-viral Gene Therapy", K. Taira, K. Kataoka, T. Niidome (editors), Springer-Verlag Tokyo, 2005, ISBN 4-431-25122-7; Zhu et al., Chinese Science Bulletin, December 2007, vol. 52 (23), pp. 3207-3215; and Varma et al., Carbohydrate Polymers 55 (2004) 77-93

Chitosans with any degree of deacetylation (DDA) greater than 50% are used in the present invention, with functionalization between 1% and 50%. (Percent functionalization is determined relative to the number of free amino moieties on the chitosan polymer.) The degrees of deacetylation and functionalization impart a specific charge density to the functionalized chitosan derivative. The resulting charge density affects solubility, nucleic acid binding and subsequent release, and interaction with mammalian cell membranes. Thus, in accordance with the present invention, these properties must be optimized for optimal efficacy. Exemplary chitosan derivatives are described in Baker et al; Ser. No. 11/657,382 filed on Jan. 24, 2007, which is incorporated by reference herein by reference. In one embodiment, the dually derivatized chitosan described herein comprises chitosan having a degree of deacetylation of at least 50%. In one embodiment, the degree of deacetylation is at least 60%, more preferably at least 70%, more preferably at least 80%, more preferably at least 90%, and most preferably at least 95%. In a preferred embodiment, the dually derivatized chitosan described herein comprises chitosan having a degree of deacetylation of at least 98%.

The chitosan derivatives described herein have a range of average molecular weights that are soluble at neutral and physiological pH, and include for the purposes of this invention molecular weights ranging from 3-110 kDa. Embodiments described herein feature lower average molecular weight of derivatized chitosans (<25 kDa, e.g., from about 5 kDa to about 25 kDa), which can have desirable delivery and transfection properties, and are small in size and have favorable solubility. A lower average molecular weight derivatized chitosan is generally more soluble than one with a higher molecular weight, the former thus producing a nucleic acid/chitosan complex that will release more easily the nucleic acid and provide increased transfection of cells.

In a preferred embodiment, administration of an expression vector comprising a PD-L1 nucleic acid is accomplished using chitosan or a chitosan derivative as the nucleic acid delivery vehicle. The chitosan derivatives described herein are generated by functionalizing the resulting free amino groups with positively charged and/or hydrophilic moieties. The derivatized chitosans described in International Patent Application Nos. PCT/CA2013/050218 and PCT/CA2014/050921, the contents of which are herein incorporated by reference in their entirety, have a number of properties which are advantageous for a nucleic acid delivery vehicle including: they effectively bind and complex the negatively charged nucleic acids, they can be formed into nanoparticles of a controllable size, they can be taken up by the cells and they can release the nucleic acids at the appropriate time within the cells.

In preferred embodiments, "dually derivatized-chitosan" or "DD-chitosan" is used, which refers to chitosan that has been dually functionalized ("dually functionalized-chitosan" or "DF-chitosan), e.g., coupled with both a Arg and a hydrophilic polyol, both of which are covalently attached to chitosan. The Arg may be covalently attached to chitosan either as single amino acid or as a polypeptide. The hydrophilic polyol may be a sugar such as glucose. By "DD-chitosan nucleic acid polyplex" or its grammatical equivalents is meant a complex comprising a plurality of DD-chitosan molecules and a plurality of nucleic acid molecules coding for PD-L1 or fragments thereof. In a preferred embodiment, the dually derivatized-chitosan is complexed with said nucleic acid coding for a PD-L1 polypeptide.

The DD-chitosan PD-L1 nucleic acid polyplexes comprise a PD-L1 nucleic acid component and a DD-chitosan component. Chitosan, and DD-chitosan nucleic acid polyplexes may be prepared by any method known in the art. For example, functionalized chitosan and nucleotide feedstock concentrations may be adjusted to accommodate various amine-to-phosphate ratios (N/P), mixing ratios and target nucleotide concentrations. A preferred method for polyplex formation is disclosed in WO 2009/039657, which is expressly incorporated herein in its entirety by reference.

Expression Vectors and Expression Control Regions

The present invention relates to expression vectors comprising a PD-L1 nucleic acid, a promoter, and transcriptional and translational stop signals. The various nucleotide and control sequences may be joined together to produce an expression vector that may include one or more convenient restriction sites to allow for insertion or substitution of the nucleic acid encoding for PD-L1 at such sites. Alternatively, the PD-L1 nucleic acid may be expressed by inserting the polynucleotide or a nucleic acid construct comprising the PD-L1 nucleic acid into an appropriate vector for expression. In creating the expression vector, the coding sequence for PD-L1 is located in the vector such that it is operably linked with the appropriate control sequences for expression.

The expression vector may be any vector (e.g., a plasmid or virus) that can be conveniently subjected to recombinant DNA procedures and can bring about expression of the nucleic acid. The choice of the vector will typically depend on the compatibility of the vector with the host cell into which the vector is to be introduced. The vector may be a linear or closed circular plasmid. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total nucleci acid to be introduced into the genome of the host cell, or a transposon, may be used.

The vector may optionally include one or more selectable markers that permit easy selection of transformed, transfected, transduced, or the like cells. A selectable marker is a gene the product of which provides for biocide or viral resistance, resistance to heavy metals, prototrophy to auxotrophs, and the like. For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

In preferred embodiments, the expression vectors of the present invention comprise a nucleic acid molecule encoding for PD-L1 or fragments thereof, comprising an expression control region operably linked to a coding region for a PD-L1 polypeptide as described herein. In some embodiments, the nucleic acid is DNA or RNA, e.g., mRNA. In some embodiments, the PD-L1 nucleic acid is an artificial nucleic acid. Preferred artificial nucleic acids include, but are not limited to, peptide nucleic acid (PNA), phosphorodiamidate morpholino oligo (PMO), locked nucleic acid (LNA), glycol nucleic acid (GNA) and threose nucleic acid (TNA).

In one specific embodiment, the expression vector is pVAX_hPD-L1 as exemplified herein (FIG. 1). In another specific embodiment, the expression vector is pVax hPD-L1 Fc (FIG. 2).

In some embodiments, the expression control region possesses constitutive activity. In a number of preferred embodiments, the expression control region does not have constitutive activity. This provides for the dynamic expression of the PD-L1 nucleic acid. By "dynamic" expression is meant expression that changes over time. Dynamic expression may include several such periods of low or absent expression separated by periods of detectable expression. In a number of preferred embodiments, the PD-L1 nucleic acid is operably linked to a regulatable promoter. This provides for the regulatable expression of the nucleic acid molecule. Expression control regions comprise regulatory polynucleotides (sometimes referred to herein as elements), such as promoters and enhancers, which influence expression of an operably linked PD-L1 nucleic acid.

Expression control elements included herein can be from bacteria, yeast, plant, or animal (mammalian or non-mammalian). Expression control regions include full-length promoter sequences, such as native promoter and enhancer elements, as well as subsequences or polynucleotide variants that retain all or part of full-length or non-variant function (e.g., retain some amount of nutrient regulation or cell/tissue-specific expression). As used herein, the term "functional" and grammatical variants thereof, when used in reference to a nucleic acid sequence, subsequence or fragment, means that the sequence has one or more functions of native nucleic acid sequence (e.g., non-variant or unmodified sequence). As used herein, the term "variant" means a sequence substitution, deletion, or addition, or other modification (e.g., chemical derivatives such as modified forms resistant to nucleases).

As used herein, the term "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Some expression control regions confer regulatable expression to an operably linked PD-L1 nucleic acid. A signal (sometimes referred to as a stimulus) can increase or decrease expression of a PD-L1 nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

Numerous regulatable promoters are known in the art. Preferred inducible expression control regions include those comprising an inducible promoter that is stimulated with a small molecule chemical compound. In one embodiment, an expression control region is responsive to a chemical that is orally deliverable but not normally found in food. Particular examples can be found, for example, in U.S. Pat. Nos. 5,989,910; 5,935,934; 6,015,709; and 6,004,941, all of which are incorporated herein by reference in their entirety.

In one embodiment, the expression vector further comprises an integration sequence. In one embodiment, the expression vector comprises a single integration sequence. In another embodiment, the expression vector comprises a first and a second integration sequence for integrating the PD-L1 nucleic acid or a portion thereof into the genome of a target cell. In a preferred embodiment, the integration sequence(s) is functional in combination with a means for integration that is selected from the group consisting of mariner, sleeping beauty, FLP, Cre, ΦC31, R, lambda, and means for integration from integrating viruses such as AAV, retroviruses, and lentiviruses.

In one embodiment, the subject composition further comprises a non-therapeutic construct in addition to the PD-L1 construct, wherein the non-therapeutic construct comprises a nucleic acid sequence encoding a means for integration operably linked to a second expression control region. This second expression control region and the expression control region operably linked to the PD-L1 nucleic acid may be the same or different. The encoded means for integration is preferably selected from the group consisting of mariner, sleeping beauty, FLP, Cre, ΦC31, R, lambda, and means for integration from integrating viruses such as AAV, retroviruses, and lentiviruses.

The procedures used to ligate the elements described above to construct the recombinant expression vectors of the present invention are well known to one skilled in the art see, e.g., Sambrook et al., 1989, supra). For further teaching, see WO2008020318, which is expressly incorporated herein in its entirety by reference.

Pharmaceutical Formulations

The present invention also provides "pharmaceutically acceptable" or "physiologically acceptable" formulations comprising DD-chitosan nucleic acid polyplex compositions of the invention. Such formulations can be administered in vivo to a subject in order to practice treatment methods.

As used herein, the terms "pharmaceutically acceptable" and "physiologically acceptable" refer to carriers, diluents, excipients and the like that can be administered to a subject, preferably without producing excessive adverse side-effects (e.g., nausea, abdominal pain, headaches, etc.). Such preparations for administration include sterile aqueous or non-aqueous solutions, suspensions, and emulsions.

Pharmaceutical formulations can be made from carriers, diluents, excipients, solvents, dispersion media, coatings, antibacterial and antifungal agents, isotonic and absorption delaying agents, and the like, compatible with administration to a subject. Such formulations can be contained in a tablet (coated or uncoated), capsule (hard or soft), microbead, emulsion, powder, granule, crystal, suspension, syrup or elixir. Supplementary active compounds and preservatives, among other additives, may also be present, for example, antimicrobials, anti-oxidants, chelating agents, and inert gases and the like.

Excipients can include a salt, an isotonic agent, a serum protein, a buffer or other pH-controlling agent, an antioxidant, a thickener, an uncharged polymer, a preservative or a cryoprotectant. xcipients used in compositions of the invention may further include an isotonic agent and a buffer or other pH-controlling agent. These excipients may be added for the attainment of preferred ranges of pH (about 6.0-8.0) and osmolarity (about 50-400 mmol/L). Examples of suitable buffers are acetate, borate, carbonate, citrate, phosphate and sulfonated organic molecule buffer. Such buffers may be present in a composition in concentrations from 0.01 to 1.0% (w/v). An isotonic agent may be selected from any of those known in the art, e.g. mannitol, dextrose, glucose and sodium chloride, or other electrolytes. Preferably, the isotonic agent is glucose or sodium chloride. The isotonic agents may be used in amounts that impart to the composition the same or a similar osmotic pressure as that of the biological environment into which it is introduced. The concentration of isotonic agent in the composition will depend upon the nature of the particular isotonic agent used and may range from about 0.1 to 10%. When glucose is used, it is preferably used in a concentration of from 1 to 5% w/v, more particularly 5% w/v. When the isotonic agent is sodium chloride, it is preferably employed in amounts of up to 1% w/v, in particular 0.9% w/v. The compositions of the invention may further contain a preservative. Examples preservatives are polyhexamethylene-biguanidine, benzalkonium chloride, stabilized oxychloro complexes (such as those known as Purite®), phenylmercuric acetate, chlorobutanol, sorbic acid, chlorhexidine, benzyl alcohol, parabens, and thimerosal. Typically, such preservatives are present at concentrations from about 0.001 to 1.0%. Furthermore, the compositions of the invention may also contain a cryopreservative agent. Preferred cryopreservatives are glucose, sucrose, mannitol, lactose, trehalose, sorbitol, colloidal silicon dioxide, dextran of molecular weight preferable below 100,000 g/mol, glycerol, and polyethylene glycols of molecular weights below 100,000 g/mol or mixtures thereof. Most preferred are glucose, trehalose and polyethylene glycol. Typically, such cryopreservatives are present at concentrations from about 0.01 to 10%.

A pharmaceutical formulation can be formulated to be compatible with its intended route of administration. For example, for oral administration, a composition can be incorporated with excipients and used in the form of tablets, troches, capsules, e.g., gelatin capsules, or coatings, e.g., enteric coatings (Eudragit® or Sureteric®). Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or other stearates; a glidant such as colloidal silicon dioxide; a sweetening agent such as sucrose or saccharin; or a flavoring agent such as peppermint, methyl salicylate, or flavoring.

Formulations can also include carriers to protect the composition against rapid degradation or elimination from the body, such as a controlled release formulation, including implants and microencapsulated delivery systems. For example, a time delay material such as glyceryl monostearate or glyceryl stearate alone, or in combination with a wax, may be employed.

Suppositories and other rectally administrable formulations (e.g., those administrable by enema) are also contemplated. Further regarding rectal delivery, see, for example, Song et al., Mucosal drug delivery: membranes, methodologies, and applications, Crit. Rev. Ther. Drug. Carrier Syst., 21:195-256, 2004; Wearley, Recent progress in protein and peptide delivery by noninvasive routes, Crit. Rev. Ther. Drug. Carrier Syst., 8:331-394, 1991.

Additional pharmaceutical formulations appropriate for administration are known in the art and are applicable in the methods and compositions of the invention (see, e.g., Remington's Pharmaceutical Sciences (1990) 18th ed., Mack Publishing Co., Easton, Pa.; The Merck Index (1996) 12th ed., Merck Publishing Group, Whitehouse, N.J.; and Pharmaceutical Principles of Solid Dosage Forms, Technonic Publishing Co., Inc., Lancaster, Pa., (1993)).

Intestinal Administration

The subject compositions may be administered orally. Oral administration may involve swallowing, so that the compound enters the gastrointestinal tract. Compositions of the invention may also be administered directly to the gastrointestinal tract. Syringes, endoscopes, cannulas, intubation tubes, catheters and other articles may be used for such administration.

Formulations suitable for oral administration include solid formulations such as tablets, capsules, coated capsules containing particulates or coated particulates, liquids, or powders, lozenges (including liquid-filled), chews, multi- and nano-particulates, gels, films, ovules, and sprays.

Liquid formulations include suspensions, solutions, syrups and elixirs. Liquid formulations may be prepared by the reconstitution of a solid.

Tablet dosage forms generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a film-forming polymer, a binder, a solvent, a humectant, a plasticiser, a stabiliser or emulsifier, a viscosity-modifying agent and a solvent. Some components of the formulation may perform more than one function.

Also included in the invention are multiparticulate beads comprising a composition of the invention.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Other suitable release technologies such as high energy dispersions and osmotic and coated particles are known.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The doses or "effective amount" for treating a subject are preferably sufficient to ameliorate one, several or all of the symptoms of the condition, to a measurable or detectable extent, although preventing or inhibiting a progression or worsening of the inflammatory disorder or condition, or a symptom, is a satisfactory outcome. Thus, the amount of PD-L1 protein produced to ameliorate a condition treatable by a method of the invention will depend on the condition and the desired outcome and can be readily ascertained by the skilled artisan. Appropriate amounts will depend upon the condition treated, the therapeutic effect desired, as well as the individual subject (e.g., the bioavailability within the subject, gender, age, etc.). The effective amount can be ascertained by measuring relevant physiological effects.

Veterinary applications are also contemplated by the present invention. Accordingly, in one embodiment, the invention provides methods of treating non-human mammals, which involve administering a chitosan-based nanoparticle of the invention to a non-human mammal in need of treatment.

Methods of Treatment

The subject compositions and methods find advantageous use in modulating inflammation. For example, the therapeutic polypeptide may inhibit the proliferation and differentiation of cells involved in an inflammatory response. These molecules can be used to treat inflammatory conditions, both chronic and acute conditions, including inflammation associated with infection (e.g. septic shock, sepsis, or systemic inflammatory response syndrome (SIRS)), ischemia-reperfusion injury, endotoxin lethality, inflammatory bowel disease (IBD), Crohn's disease, colitis, or resulting from over production of cytokines (e.g. TNF or IL-1.) Inflammatory disorders of particular interest for treatment in the present invention include, but are not limited to, Crohn's disease, and inflammatory bowel disease.

A therapeutic composition of the present invention may also be used to treat and/or prevent organ rejection or graft-versus-host disease (GvHD). Organ rejection occurs by host immune cell destruction of the transplanted tissue through an immune response. Similarly, an immune response is also involved in GvHD, but, in this case, the foreign transplanted immune cells destroy the host tissues. The administration of a therapeutic composition of the present invention that inhibits an immune response, particularly the proliferation, differentiation, or chemotaxis of T-cells, may be an effective therapy in preventing organ rejection or GvHD.

The examples set out herein illustrate several embodiments of the present disclosure but should not be construed as limiting the scope of the present disclosure in any manner.

EXAMPLES

Example 1

Plasmid Construction and Production

Both optimized PD-L1 and PD-L1-Fc DNA sequences were cloned in pVAX backbone cloning vector. Plasmid contain a plasmid replication origin (pUC ori) under the control of a human cytomegalovirus immediate-early gene promoter (CMV) and with a kanamycin resistance gene (KAN). Designed plasmids were custom synthesized by DNA 2.0 (Newark, Calif.). Once received, DNA was reconstituted according to the manufacturer's recommendation. Briefly absorbent paper containing the DNA was put into a small 0.2 mL tube with perforated bottom (performed with 23G needle). The small tube was then put into a larger 1.5 mL tube. 200 µL of water was added to the absorbent paper, after 1 min incubation @ RT, the tube was centrifuged at maximum speed for 1 min. Solubilized DNA was recovered in the 1.5 ml tube. The DNA was then used to transform *E. coli* DH5α, chemically competent bacteria. Briefly, to a 100 µl thawed *E. coli* DH5α cells 10 µL of the eluted DNA was added in a sterile condition. After 30 mins incubation on ice, cells were heat shocked at 42 C for 30 secs and incubated on ice for 2 min. 30 µL of Luria-Bertani (LB) medium was added to the DH5α transformed cells and incubated for 1 hour at 37 C under 180 rpm shaking. The culture is then plated on a LB-agar plate containing kanamycin (50 µg/ml) and incubated for 16 h at 37 C. The next day, a single isolated colony was used to inoculate 6 mL of LB Broth containing kanamycin (50 µg/ml). The culture was incubated on a shaker (180 rpm) at 37 C for 5-6 hours. The culture was subsequently used to inoculate 2.5 L of LB medium which was incubated at 37 C for 16 hours on shaker. Plasmid DNA was then isolated from this large bacterial culture using EndoFree Plasmid Giga Kit (QIAGEN) according to the manufacturer's instruction. Upon isolation PD-L1 and PD-L1-Fc DNA insert within the plasmid was verified using restriction enzymes and fragment size confirmed by agarose gel Example 2

In Vitro PD-L1 and PD-L1-Fc Expression

To measure in vitro expression from the polyplex, HEK-293T cells were seeded in 6-well tissue culture plates at a density of 800,000 cells per well in high glucose DMEM complete media (10% Fetal Bovine Serum, 50 Units/ml penicillin, 50 µg/ml streptomycin) and incubated overnight at 37° C. and 5% $CO_2$. The following day, PD-L1-Fc polyplex was thawed briefly in a 37° C. water bath. Each polyplex was diluted in sterile water to a concentration of 12.5-200 µg/ml of DNA, corresponding to 0.5-8 µg of DNA per well, and kept on ice until transfection. HEK-293T supernatant was removed from each well and cells were gently washed with 2 ml of pre-warmed OptiMEM. 1 ml of pre-warmed OptiMEM was gently added to each well. 40 µl of diluted polyplex was added to the well and the plate was gently swirled to ensure proper mixing. The cells were incubated for 3 hours at 37° C. and 5% $CO_2$. Following incubation, the cell culture medium was removed by pipetting and replaced with 2 ml of pre-warmed DMEM complete medium and the cells were incubated at 37° C. and 5% $CO_2$ for 48 hours. At 48 hours post-transfection, the cell culture medium was removed from wells transfected with PD-L1-Fc polyplex or untransfected cells as a control. Cell debris was removed from the supernatant by centrifugation (1500 rpm, 5 min, 4° C.) and the supernatant was stored at −80° C. until analysis. To quantify the total cellular protein, cell culture supernatant was removed from the wells, the transfected cells were washed with cold PBS, and 500 µl of lysis buffer (50 mM Tris pH 8.0, 1% TritonX-100, 100 mM NaCl, 1 mM EDTA, 10% glycerol plus cOmplete Protease Inhibitor Cocktail) was added to the wells. The plate was left on ice for 2-3 minutes and cells were collected using a cell scraper, transferred to a 1.5 ml microcentrifuge tube and left on ice for 30 min. Cell debris was removed from the lysate by centrifugation (13000 rpm, 10 min, 4° C.) and total protein was measured by Lowry assay.

The PD-L1 protein concentration was measured by ELISA, as per the manufacturer's protocol. Briefly, 96 well plates were coated with anti-human PD-L1 capture antibody and incubated overnight at 25° C. The following day, plates were washed with 0.05% Tweeen® 20 in PBS, blocked with 1% bovine serum albumin (BSA) in PBS for 1 hour and followed by an additional wash step. Samples or standards were added to the plate and incubated at 25° C. for 2 hours. A biotinylated goat anti-human PD-L1 detection antibody was added to the wells for 2 hours, followed by washes and the addition of streptavidin-HRP for 20 min. The wells were washed and a tetramethylbenzidine solution was added for 20 min to detect HRP. The reaction was terminated by the addition of 2 N sulfuric acid and plates were read on a SpectraMAX Plus (ENG0214) using the SoftMax Pro software at 450 nm. PD-L1 protein levels were calculated using lyophilized standard protein provided by the manufacturer. Protein samples were fitted to a standard 4 parameter logistic curve. In some instances, the PD-L1 protein levels were normalized to total protein in the transfected cells and represented as ng of PD-L1-Fc/mg of total cellular protein.

Figures 4A, 4B:
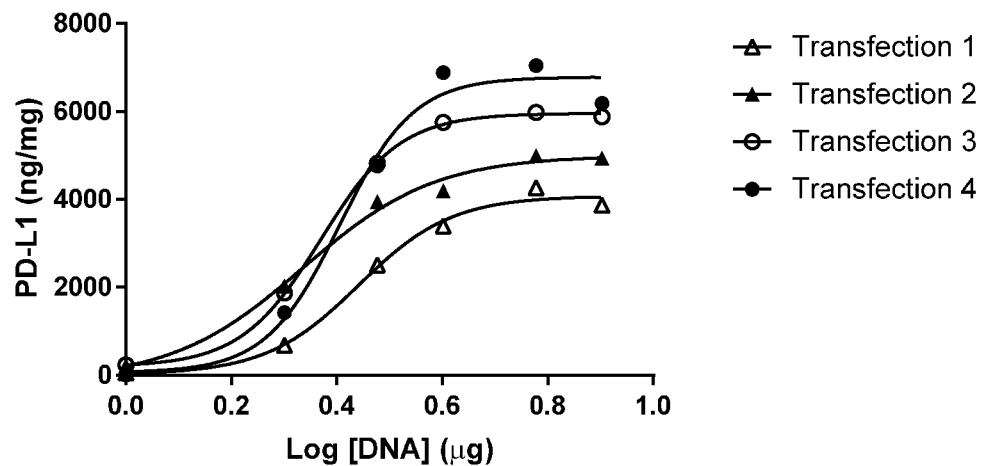
FIG. 4: In vitro expression of PD-L1-Fc from polyplex transfection. (A-B) HEK-293T were transfected with PD-L1-Fc polyplexes containing increasing concentrations of pVAX-opt-hPD-L1-Fc DNA, as indicated. (A) Supernatants were collected at 48 hours post-transfection and assayed for hPD-L1-Fc protein by ELISA. Data were normalized to total cellular protein. (B) Table of EC50 and maximum protein expression.
Figure 5A:
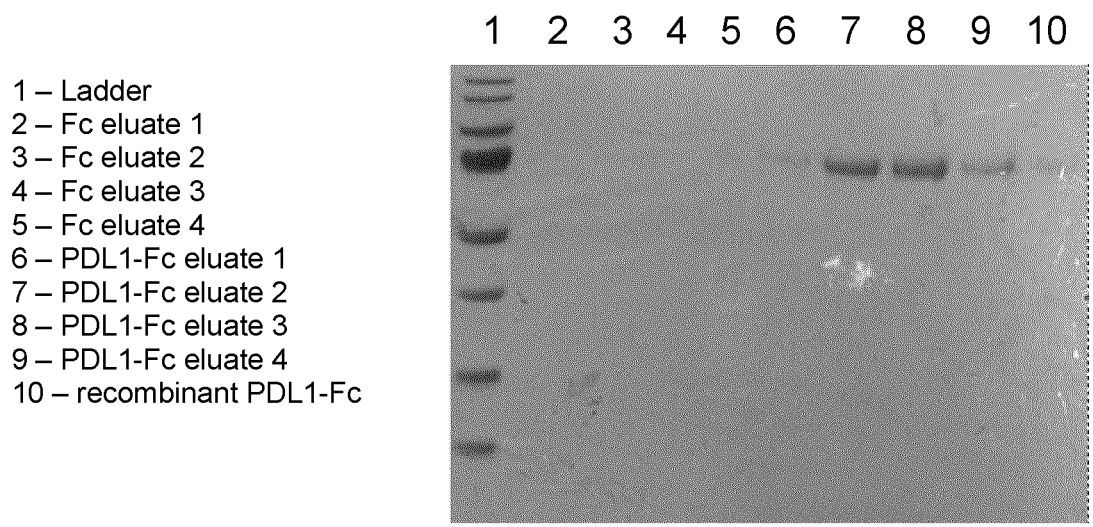
FIG. 5: Purification of in vitro-generated Fc-fused constructs and expression. (A) Protein expression confirmed by coomassie gel staining: HEK293T cells were transfected with Fc control or PD-L1-Fc plasmid DNA using Lipofectamine 2000 (Invitrogen). Cell culture medium was exchanged for serum-free medium 24 h post-transfection. Cell culture supernatant was collected 72 h post-transfection and Fc-fused proteins were purified using Protein G HiTrap columns (GE). Buffer was exchanged for PBS using PD-10 desalting columns (GE), and protein was eluted in four equal fractions (eluate 1-4). (B) HEK293T cells were transfected with Fc control or PD-L1-Fc plasmid DNA using Lipofectamine 2000 (Invitrogen). Cell culture medium was exchanged for serum-free medium 24 h post-transfection. Cell culture supernatant was collected 72 h post-transfection and Fc-fused proteins were purified using Protein G HiTrap columns (GE). Buffer was exchanged for PBS using PD-10 desalting columns (GE), and protein was eluted in four equal fractions (F1-4). PD-L1 protein concentration was determined by ELISA. (C) NIH/3T3 cells were transfected with wild-type PD-L1 plasmid DNA or control (pVax) using Lipofectamine 2000 (Invitrogen) in a 6-well plate. Cells were washed and re-seeded in a 96-well flat-bottomed plate 24 h post-transfection. The following day (Day 2), and on the 3 subsequent days, PD-L1 expression at the cell surface was analyzed by flow cytometry. (D) NIH/3T3 cells were transfected with wild-type PD-L1 plasmid DNA or control (pVax) using Lipofectamine 2000 (Invitrogen) in a 6-well plate. Cells were washed and re-seeded in a 96-well flat-bottomed plate 24 h post-transfection. The following day (Day 2), and on the 3 subsequent days, PD-L1 expression levels at the cell surface was analyzed by flow cytometry.
Figure 5B:
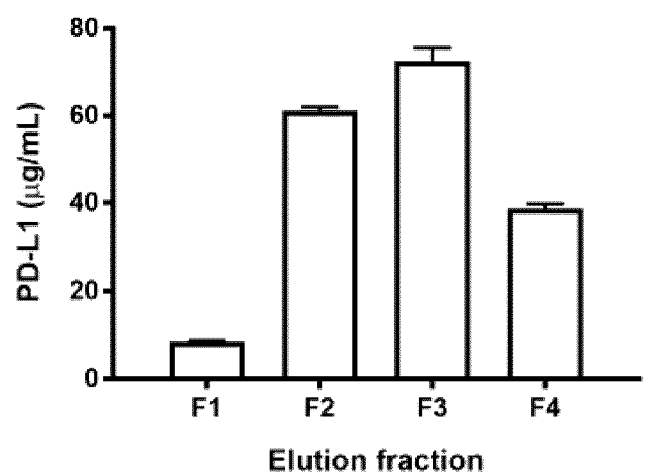
Figure 5C:
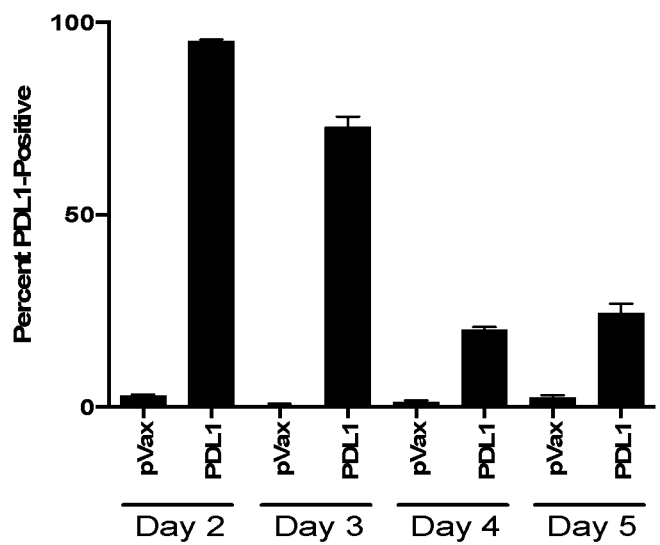
Figure 5D:
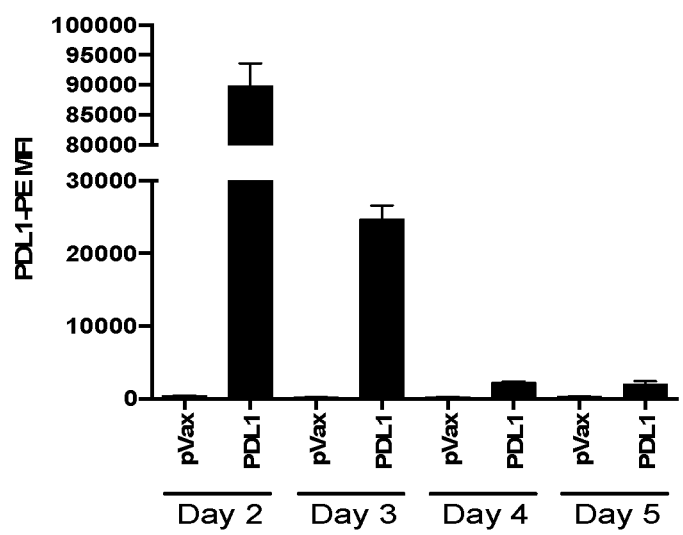

To assess the transfection potency of PD-L1-Fc polyplexes, HEK-293T were transfected with increasing amounts of DNA contained within the DD-X polymer. The quantification of PD-L1 protein showed a dose-dependent increase in hPD-L1-Fc expression with increasing amounts of pVAX-opt-hPD-L1-Fc plasmid DNA (FIG. 4A). The EC50 was similar between independent transfections, although the maximum expression of PD-L1-Fc (ng/mg) showed some variability between transfections (FIG. 4B).

Example 3

Purification of Fc-Fused Protein (PD-L1-Fc)

HEK293T cells were plated in T75 flasks at 5×10⁶ cells/flask in DMEM (10% FBS, Multicell) and incubated at 37 C. The following day, cells were transfected with PD-L1-Fc plasmid DNA (9 ug/flask; 3 ml per flask) using Lipofectamine 2000 (Invitrogen), as recommended by the manufacturer, and incubated at 37° C. After 24 h, DMEM medium was exchanged with 12 ml EXCELL serum-free medium (Sigma Aldrich). After 48 h (72 h post transfection), supernatant was collected and stored at −20° C. until purification. Fc-fused proteins were purified using Protein G HiTrap columns (GE), as recommended by the manufacturer. Buffer was then exchanged using PD-10 desalting columns, and protein was eluted in 4 fractions of PBS (Gibco). Presence of protein was detected by Coomassie stain. PDL1 concentration in each of the fractions was measured by ELISA (Duoset, R&D), as recommended by the manufacturer.

Example 4

In Vitro PD-L1-Fc Functionality Assay

To assess functionality of Fc-fused PD-L1 construct, anti-mouse CD3 (0.2 μg/ml, eBioscience) and/or anti-mouse CD28 (1 μg/ml, eBioscience) with or without 5 μg/ml in vitro serum free media produced PDL1-Fc or commercial rhPDL1-Fc (Adipogen) were added to wells of a 96-well flat-bottom plate in PBS (50 μl/well). rhIgG1-Fc (Adipogen) was used as a negative control.

The plate was put on plate-shaker on medium speed for 1 h and then incubated overnight at 4 C. The following day, spleens were removed from 3 mice (Jackson Laboratories). Splenocytes were isolated by grinding the spleens on the frosted ends of microscope slides. Red blood cells were lysed for 1 min in 5 ml of in house made ACK lysis buffer, and the lysis was stopped by adding 45 ml PBS (10% FBS). After centrifugation and decanting, cells from the 3 mice were resuspended in supplemented RPMI medium (10% FBS, NEAA, L-glutamine, 2-ME; Multicell), pooled, counted, and adjusted to an appropriate concentration. A portion of cells were stained with CellTrace Violet (Life Technologies), as recommended by the manufacturer. The PBS was removed from the aCD3/aCD28 96-well plate carefully by pipetting. Cells were then seeded into the wells in the RPMI medium (200,000 cells/well), and incubated at 37 C for 3 or 4 days. At either time point, the cells were transferred to a new 96-well v-bottom plate and stained with a fixable viability dye (eBioscience) for 30 mins in the dark and on ice. Cells were washed twice with cold FACS buffer (PBS 2% FBS) and acquired on the flow cytometer (BD LSR II). Cell proliferation was measured by monitoring cell division peaks in the CellTrace Violet channel. Cell activation was measured by detecting cell size in the FSC-SSC gate.

To determine if opt-hPD-L1-Fc binds to the human PD-1 receptor and activates an intracellular signal, the PathHunter Jurkat PD-1 (SHP2) Signaling Assay (DiscoverX) was used. Prior to testing this assay, a large-scale batch of purified PD-L1-Fc protein was generated. Briefly, PD-L1-Fc was expressed from construct by transfecting HEK-293T cells with PD-L1-Fc plasmid DNA. Briefly, 3.9×10⁵ HEK-293T cells were plated in 30 ml DMEM (Multicell) complete (10% FBS, 100 U/ml Penicillin, 100 μg/ml Streptomycin) in a T175 flask and incubated overnight at 37° C. and 5% $CO_2$. The following day, medium was aspirated from the flask and cells were washed once with 10 ml PBS (Multicell). Cells were transfected with 49 μg of PD-L1-Fc plasmid using Lipofectamine 2000 (Life Technologies; 100 μl per flask) in 5.5 ml of OptiMEM (Gibco). Cells were incubated (37° C. and 5% $CO_2$) for 2 h, and then 40 ml of DMEM complete was added to the flask. Cells were incubated for 24 h, medium was aspirated, and cells were washed with 10 ml PBS. EXCELL serum-free media (45 ml; Sigma) was added to the flask and cells were incubated at 37° C. and 5% $CO_2$. After 24 h (48 h post-transfection), supernatant was removed and centrifuged for 5 min at 1500 rpm to remove cell debris. Supernatant was transferred to a new 50 ml tube and stored at −80° C. PD-L1-Fc was purified using Protein G HiTrap columns (GE) as recommended by the manufacturer. Buffer was exchanged for PBS using PD-10 desalting columns (GE) as recommended by the manufacturer. PD-L1-Fc was stored at −80° C. until protein was concentrated and quantified. PD-L1-Fc protein was concentrated using Amicon Ultra-4 centrifugal filters (Millipore Sigma) as recommended by the manufacturer. Protein was immediately quantified by PD-L1 ELISA (R&D). In some cases, PD-L1-Fc concentration was diluted to 1 mg/mL in PBS and stored at −80° C.

To assess intracellular activation through the human PD-L1 receptor, the PathHunter cells were cultured as recommended by the manufacturer. Cells were centrifuged and re-suspended in pre-warmed AssayComplete Cell Plating Reagent. Cells were seeded into the wells of a white 96-well flat-bottomed tissue culture plate (50 μl/well; 20,000 cells/well) and incubated at room temperature for 15 min. AssayComplete Cell Plating Reagent (10 μl/well) was added to wells with or without anti-PD-1 (clone NAT105, Abcam). Purified PD-L1-Fc protein or recombinant non-lytic human IgG1-Fc (Adipogen) were prepared in AssayComplete Plating Reagent and added to the cells (50 μl/well). Cells were incubated for 40 min at 37° C. and 5% $CO_2$. PathHunter Bioassay Reagent 1 was added to the cells (10 μl/well) and the plate was placed on a plate shaker for 1 min at 350 rpm. Cells were incubated for 15 min at room temperature and in the dark. PathHunter Bioassay Reagent 2 (40 μl) was added to each well and cells were incubated for 1 hour at room temperature and in the dark. Luminescence was read on a luminometer (enSpire—Perkin Elmer). Data was analyzed as luminescence (RLU; Relative Fluorescence Units) relative to unstimulated controls. Data was presented as mean±standard deviation. Data was analyzed using a student's t test and asterisks represent statistically significant differences (*, $p \leq 0.05$; , $p \leq 0.01$; *, $p \leq 0.001$).

Figure 6A:
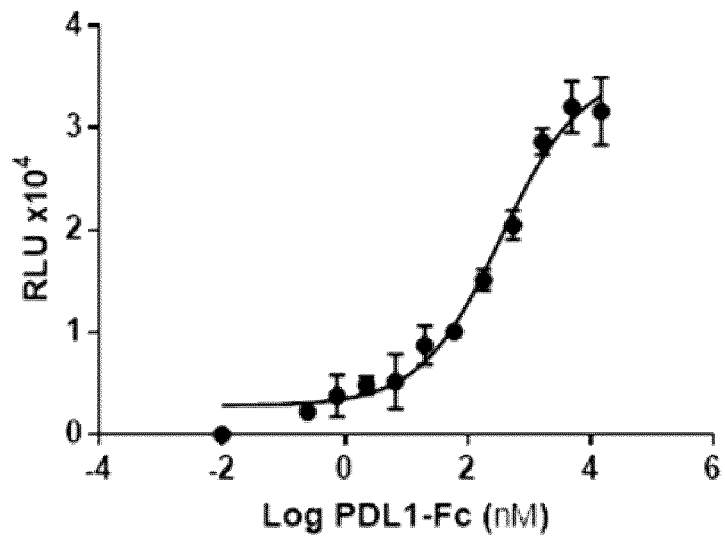
FIG. 6: Expressed PD-L1-Fc signals through the human PD-1 receptor in a dose-dependent manner. Cells were transfected with PD-L1-Fc and purified from the cell culture supernatant. (A) PathHunter PD-1 Signaling Assay cells were stimulated with increasing concentrations of PD-L1-Fc (40 min) and signal activation was measured by luminescence (RLU; Relative Luminescence Units). (B) PathHunter PD-1 Signaling Assay cells were incubated with recombinant IgG1-Fc or PD-L1-Fc (50 μg/mL, 40 min) with and without anti-PD-1 (lo: 0.1 μg/mL, hi: 1.0 μg/mL) and signal activation was measured by luminescence (RLU; Relative Luminescence Units). Cell activation was assayed in triplicate and data is presented as RLU relative to unstimulated control. Data is presented as mean±standard deviation and is representative of 4 independent experiments. Data was analyzed using a student's t test and asterisks represent statistically significant differences (*, $p \leq 0.05$; , $p \leq 0.01$; *, $p \leq 0.001$).
Figure 6B:
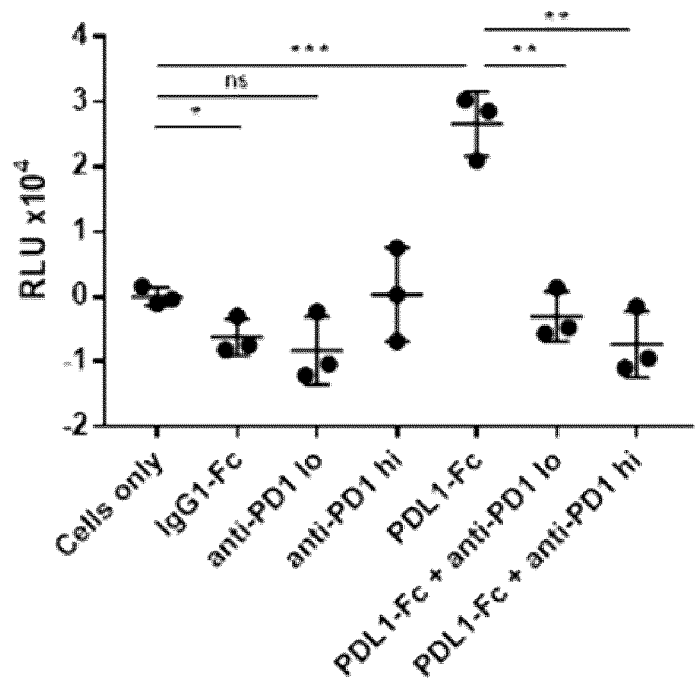
Figure 7A:
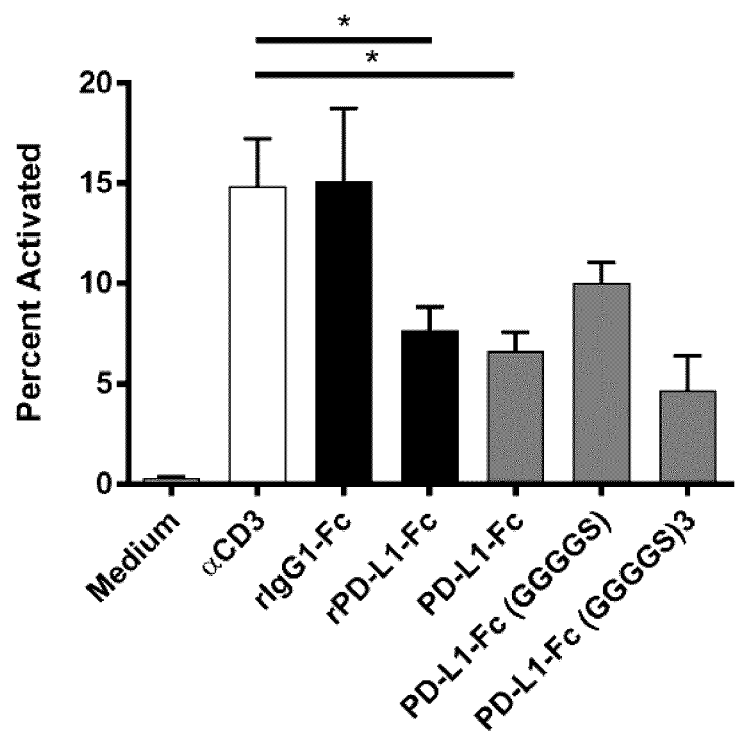
FIG. 7A discloses "GGGGS" as SEQ ID NO: 5 and "(GGGGS)3" as SEQ ID NO: 8.
Figure 8A:
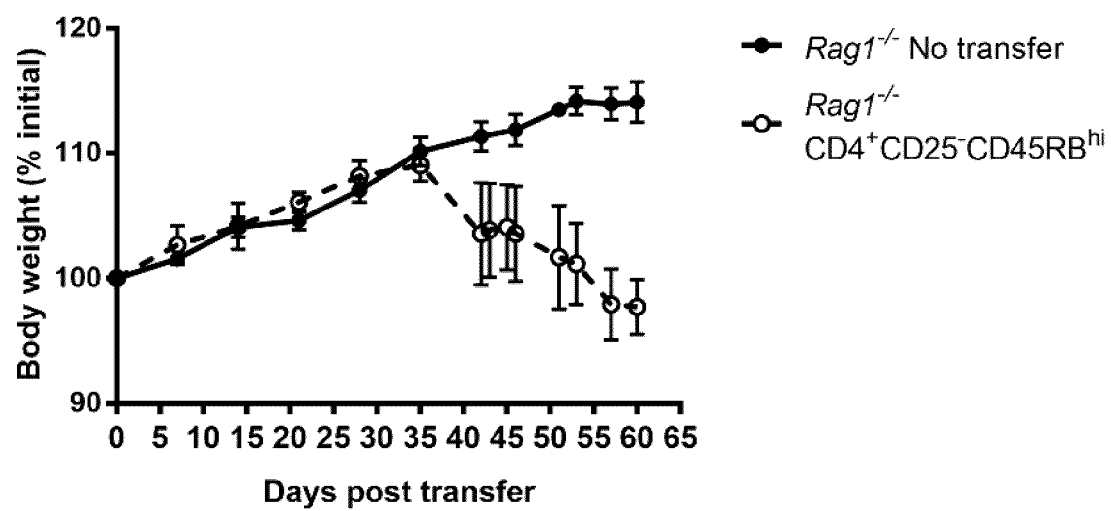
FIG. 8: Disease model optimization. (A) Male Rag1−/− mice were injected intraperitoneally with naïve T cells, defined as CD4+CD25-CD45RBhi or left untreated. Transfer of naïve T cells induced disease as observed by the bodyweight loss. (B) To induce acute graft versus host disease (GvHD), female BALB/c mice were irradiated with 700 cGY and transferred with allogeneic C57Bl6/J bone marrow (10 M cells) combined with 2.5M splenocytes. GvHD was successfully induced using these conditions as observed by the initial bodyweight loss observed within the first 10 days. Furthermore, a secondary bodyweight drop was observed starting approximately on day 20. The no transplant groups confirmed the successful irradiation and the BMT control confirms successful transfer of the allogeneic bone marrow.
Figure 8B:
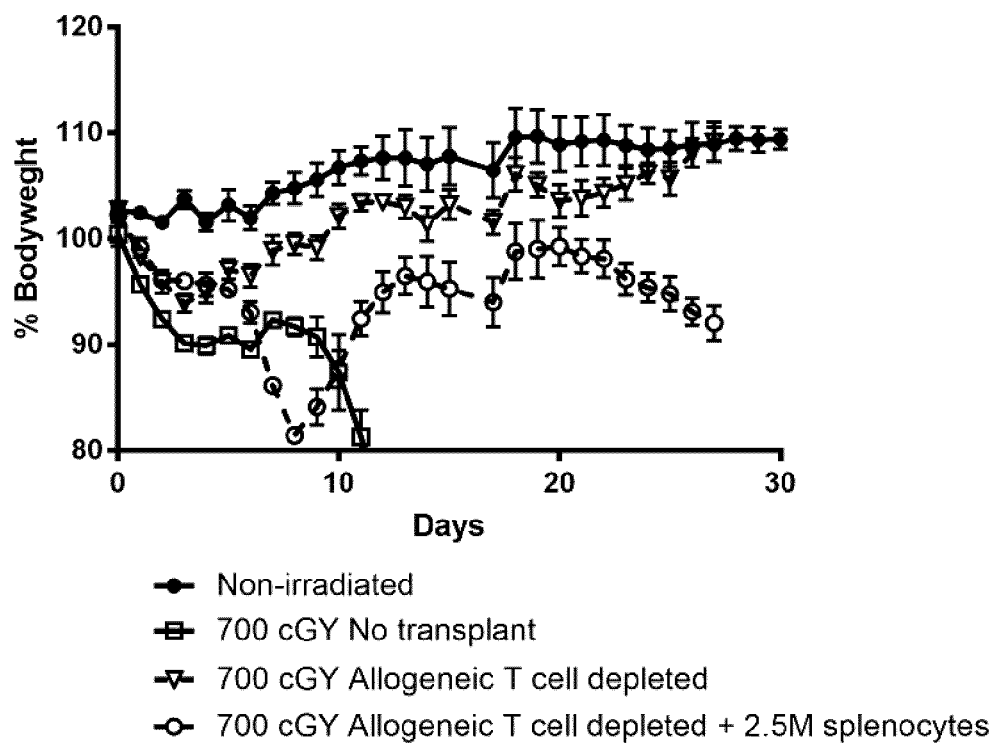

The results of the foregoing are summarized here. To determine whether protein expressed from the pVAX-opt-hPD-L1-Fc plasmid will bind to the human PD-1 receptor and initiate intracellular signaling, the PathHunter Jurkat PD-1 (SHP2) Signaling Assay (DiscoverX) was used. Signaling through the PD-1 receptor increased with increasing doses of purified PDL1-Fc and appeared to plateau at the maximum dose of 14.7 μM (783 μg/ml; FIG. 6A). To ensure that this dose-dependent induction of luminescence was due to a PDL1-PD1-specific interaction, a competition assay was utilized (FIG. 6B). Stimulation of the PathHunter cells with purified PDL1-Fc, but not recombinant IgG1-Fc, resulted in an increase in luminescence, indicating that signal induction was not caused by binding of PD-1 to the Fc fragment fused to the PD-L1 protein. Furthermore, PDL1-Fc-induced luminescence was inhibited when cells were incubated with anti-human PD-1 prior to stimulation with PD-L1-Fc, indicating that the binding and signaling through the PD-1 receptor was due to a PDL1-PD1-specific interaction.

Example 5

PD-L1 Wild-Type Membrane Bound In Vitro Expression and Functionality Assay

To determine hPD-L1 expression kinetic at the cell surface, NIH/3T3 cells were seeded (400,000 cells/well; 2 ml; DMEM 10% FBS) into a 6-well plate and incubated overnight at 37 C. The following day, cells were transfected with wild-type PD-L1 construct plasmid or pVax control with Lipofectamine 2000, as recommended by the manufacturer. Twenty-four hours after transfection, cells were washed with PBS, and resuspended by adding enzyme-free dissociation buffer (EFDB, Gibco; 2 ml/well), incubating at 37 C for 5 mins, and gently pipetting the cells off of the plate. Cells were centrifuged at 1500 rpm for 5 mins and resuspended in DMEM (10% FBS). Cells were re-seeded (10,000 cells/well) into a 96-well flat-bottomed plate, and cultured for 2-5 days. At each time point, supernatant was removed, cells were resuspended in EFDB as described above, and cells were distributed into a 96-well v-bottomed plate for FACS staining. Cells were stained with anti-human PD-L1-PE (BioLegend) at 0.2 ng/well and a fixable viability dye eFluor 780 (eBioscience) as recommended by supplier for 30 mins on ice and in the dark. Cells were washed twice, resuspended in FACS buffer, and acquired on the flow cytometer.

To test functionality of the hPD-L1 expressed at the NIH/3T3 cell surface, a PD-1 binding assay was employed. NIH/3T3 cells were transfected in 6-well plates as described above. Forty-eight hours after transfection, cells were resuspended in EFDB as described above, centrifuged, resuspended in FACS Buffer, and seeded into a 96-well v-bottomed plate. Cells were centrifuged at 1500 rpm for 5 mins, decanted, resuspended (50 μl) with or without rhPD-1 (R&D) at various concentrations, and incubated at 37 C for 30 mins. Cells were centrifuged, washed twice with FACS buffer, and stained with anti-human PDL1-PE (0.2 ng/well) or isotype control, anti-human PD-1-APC (eBioscience) at 0.8 ng/well or isotype control, and a viability dye for 30 mins on ice and in the dark. Cells were then washed twice, resuspended in FACS buffer, and acquired using BD LSR II Flow Cytometer. Data were analyzed using FlowJo 10.2 [software (Tree Star, Or. Calif.)

Example 6

In Vivo Efficacy Studies
GvHD Model 10 weeks old female BALB/c SPF mice (Charles River) received a total body irradiation of 700 cGy in split dose 2×350 cGy (RS2000 Biological Research X-ray source) first irradiation was given in the afternoon of day −1 and the second in the morning of day 0. 8-10 weeks old male C57Bl6/j mice (Charles River) were used for donor cells.

Study includes 3 control groups (n=5): non-irradiation group, no transplant group, 10 million BMT only group; and 4 treatment groups (n=8) receiving 10 million BMT and 2.5 million splenocytes. Starting from day 1, mice were treated once a week by enema for the following 6 weeks (for a total of 7 dosing) or left untreated. Animals were monitored daily for body weight and clinical signs. An animal with more than 25% body weight loss and or clinical scoring of 8 or more was terminated.

Figure 9A:
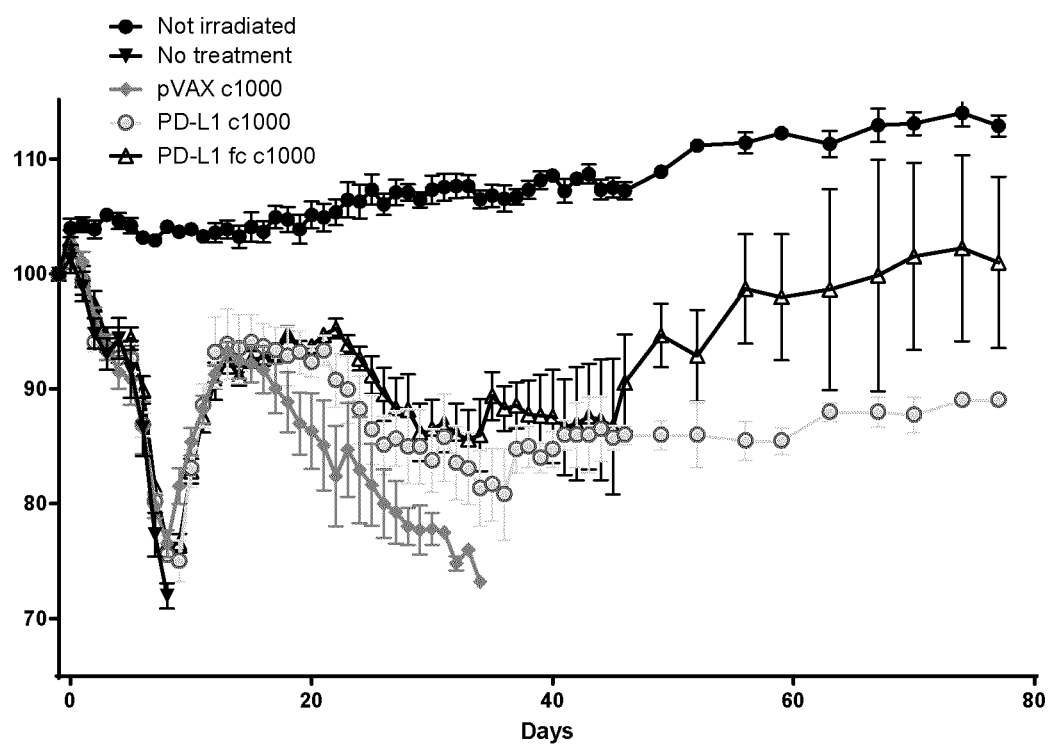
FIG. 9: Therapeutic efficacy of PD-L1 and PD-L1 Fc polyplexes in GvHD. (A) GvHD was induced as previously demonstrated in FIG. 8B. Mice were either left untreated or injected by enema weekly for 7 weeks with pVAX, PD-L1 or PD-L1 Fc polyplexes at a concentration of c1000. Animals reaching 75% of their initial bodyweight were euthanized. The bodyweight of the animals was rescued with the administration of PD-L1 and PD-L1 Fc polyplexes. (B) The clinical signs of disease were reduced in PD-L1 or PD-L1-Fc treated mice and the average clinical signs observed on day 21 were also decreased in PD-L1 and PD-L1-Fc treated mice. (C) Survival curve of mice following the induction of GvHD, all untreated and pVAX treated animals succumb to disease, approximately 40% of the PD-L1 Fc and 30% of the PD-L1, treated animals survived until day 75.
Figure 9C:
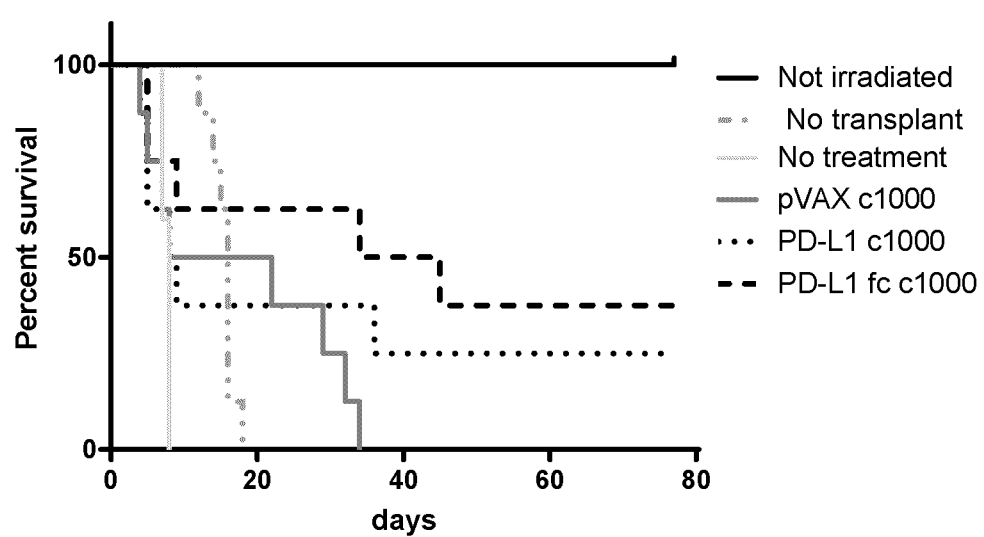
Figure 10A:
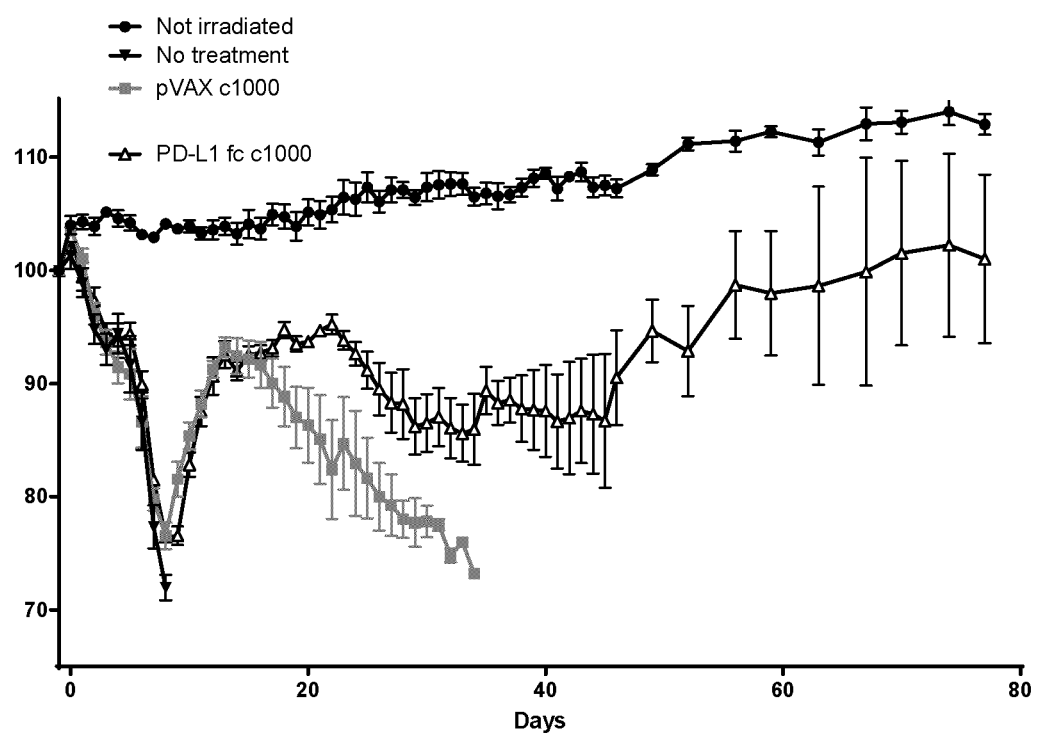
FIG. 10: Therapeutic efficacy of PD-L1 Fc and PD-L1 polyplexes in GvHD. (A) GvHD was induced as previously demonstrated in FIG. 8B. Mice were either left untreated or injected by enema weekly for 7 weeks with pVAX, or PD-L1 Fc polyplexes at a concentration of c1000. Animals reaching 75% of their initial bodyweight were euthanized. The bodyweight of the animals was rescued with the administration of PD-L1 Fc polyplexes. (B) GvHD was induced as previously demonstrated in FIG. 8B. Mice were either left untreated or injected by enema weekly for 7 weeks with pVAX, or PD-L1 polyplexes at a concentration of c1000. Animals reaching 75% of their initial bodyweight were euthanized. The bodyweight of the animals was rescued with the administration of PD-L1 polyplexes. (C) Survival curve of mice following the induction of GvHD, all pVAX treated animals succumb to disease, approximately 40% of the PD-L1 Fc and 30% of the PD-L1, treated animals survived until day 75.
Figure 10B:
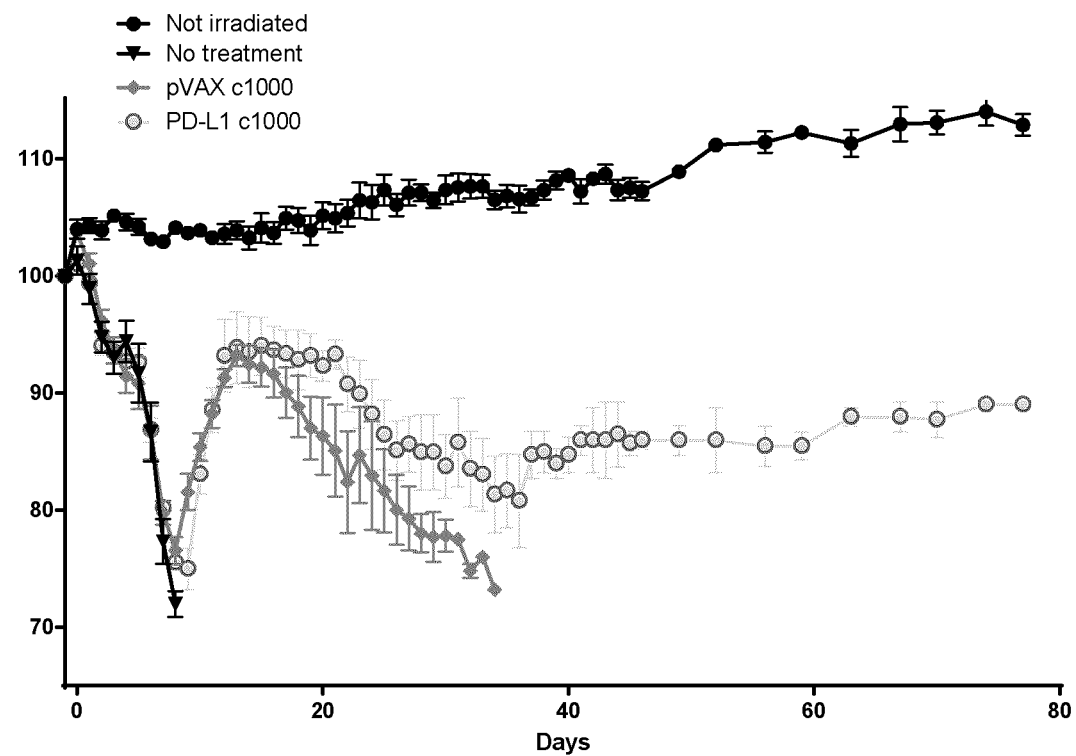
Figure 10C:
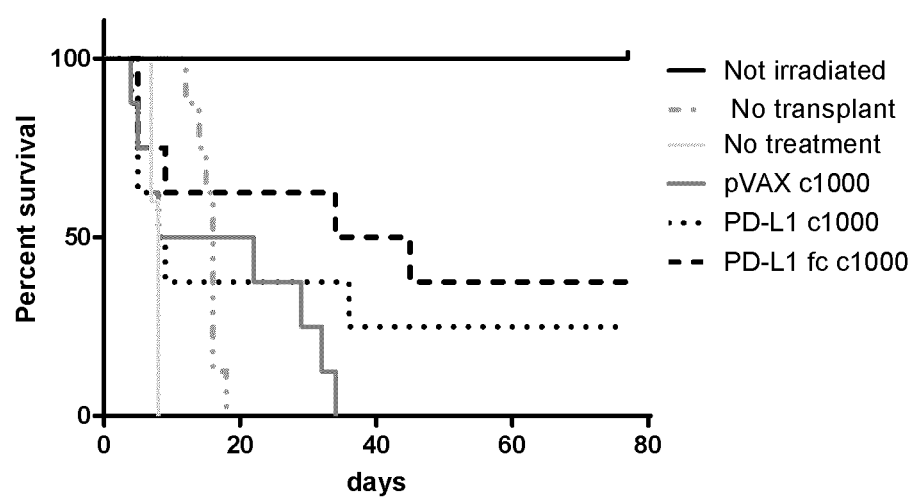
Figure 11A:
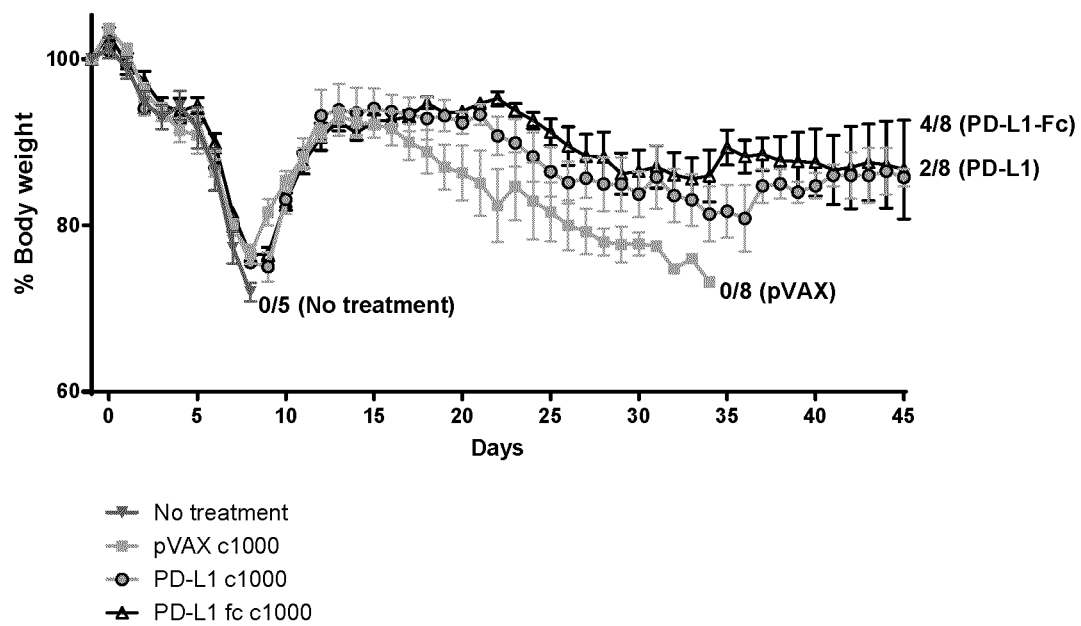
FIG. 11: Therapeutic effects of PD-L1 and PD-L1 Fc in GvHD. (A) GvHD was induced as previously demonstrated in FIG. 8B. Mice were either left untreated or injected by enema weekly for 7 weeks with pVAX, PD-L1 or PD-L1 Fc polyplexes at a concentration of c1000. The bodyweight of the PD-L1 and PD-L1 Fc treated animals was greatly improved compared with the no treatment and pVAX treated animals starting on day 18. (B) Survival curve of mice following the induction of GvHD, all pVAX treated as well as untreated animals succumb to disease. On the other hand, 50% of the animals treated with PD-L1 Fc and 25% of the animals administered with PD-L1 survive until day 45.
Figure 11B:
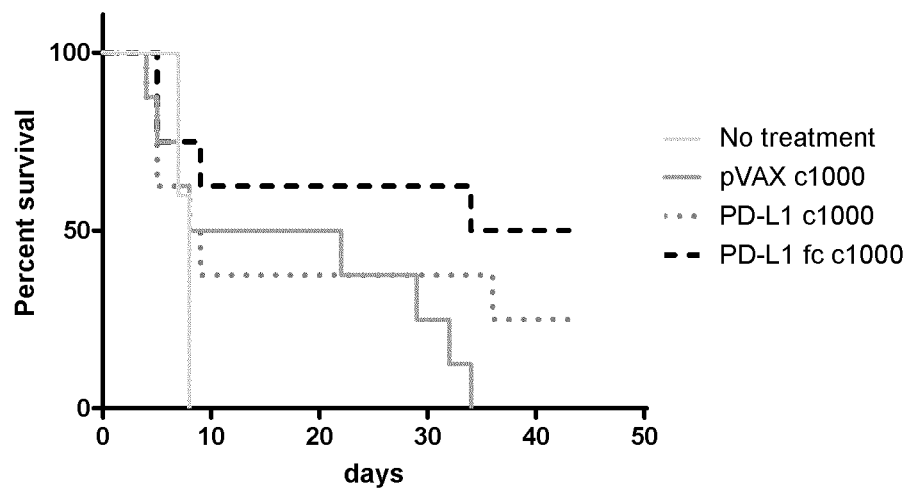
Figure 12A:
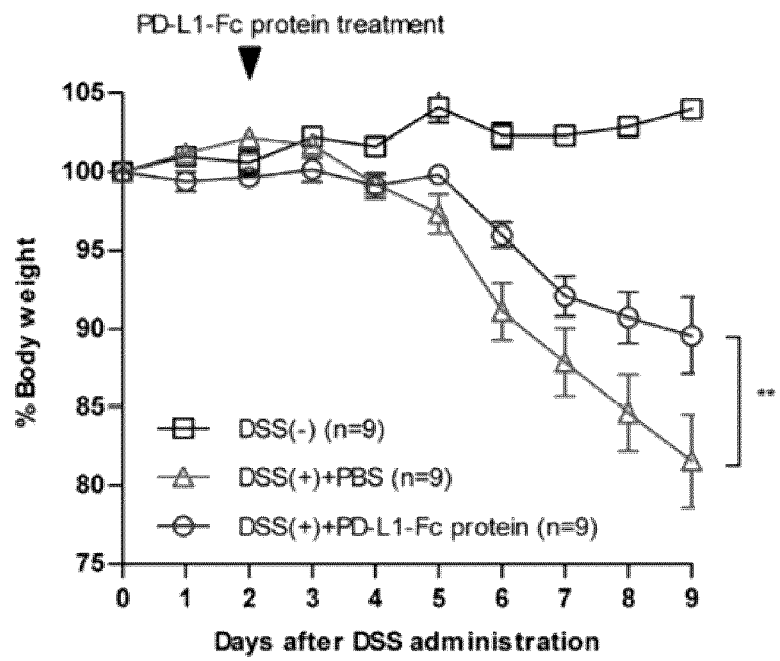
FIG. 12: Administration of recombinant PD-L1 Fc in a DSS-model of colitis. (A) Figure taken from Song et al, Gut 2015. Rag1−/− mice were administered 2% DSS in their drinking water and injected with recombinant PD-L1 Fc protein or PBS intraperitoneally on day 2. Injection of recombinant PD-L1 Fc lead to a less severe bodyweight loss compared with PBS injected animals. (B) Rag1−/− mice were administered 4% DSS in their drinking and injected intraperitoneally with recombinant PD-L1 Fc or PBS on day 3 and day 6. The bodyweight of the animals was equivalent throughout the study. However, no therapeutic effect was observed with PD-L1-Fc soluble protein and accordingly the Song et al. results were not reproduceable.
Figure 12B:
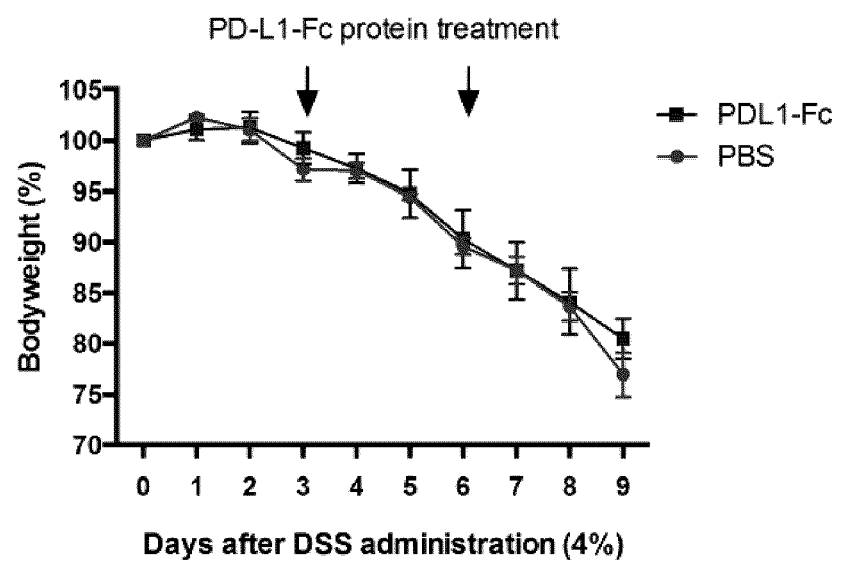

Weekly intracolonic administration of the PD-L1 or PD-L1-Fc polyplex decreased the bodyweight loss compared to pVAX control treated animals (FIGS. 9A, 10A, 10B and 11A). Mice that received PD-L1 or PD-L1-Fc also showed a reduction in the clinical signs associated with GvHD (FIG. 9B) and had improved survival relative to untreated and pVAX control treated animals (FIGS. 9C, 10C and 11B). Without being bound by theory, it is contemplated herein that as T cells traffic through the gut, they are exposed to the PD-L1 polypeptide and become "tolerized." Upon leaving the gut, the T cells go into circulation and can suppress effector T cell function. The tolerized T cells may result in upregulation of a regulatory T cell subset and/or a decrease or suppression of pathogenic effector cells. Moreover, PD-L1 has been shown to upregulate molecules that are important for epithelial repair. Without being bound by theory, it is also contemplated herein that given that there is damage to the barrier function of the gastrointestinal tract following irradiation and disease, it follows that increased PD-L1 leading to increased epithelial repair may also help restore intestinal barrier function.

Example 7

T Cell Colitis Model

Total CD4+ T cells were isolated from the spleens of 6-8-week-old female C57BL/6 mice via negative selection using the magnetic activation cell sorter (MACS) CD4 T-cell isolation kit (Miltenyi Biotec, Auburn, Calif.). Enriched cells were subsequently sorted for CD4+CD25-CD45RBhigh naive T cells using FACS (FACSAria™, BD Biosciences, San Jose, Calif.). 5×105 CD4+CD25-CD45RBhigh cells were transferred intraperitoneally (IP) to recipient 6-8-week-old female B10-RAG2-deficient mice (Jackson).

Animals bodyweight and clinical signs were monitored 2-3/week. On day 14, presence of CD4 T cell was confirmed by flow cytometry staining for CD4. Weekly enema treatment started on day 15 or 19 post T cell transfer (total of 6 or 7 treatments). Animals were monitored twice per week for body weight and clinical signs. An animal with more than 25% body weight loss or severe clinical signs is terminated.

Figure 13A:
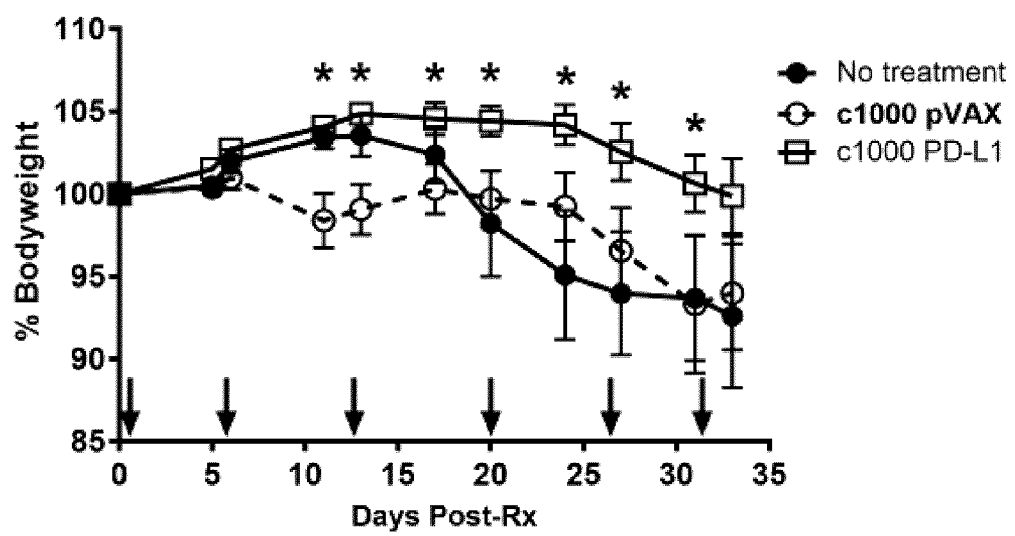
FIG. 13: Therapeutic efficacy of PD-L1 and PD-L1 Fc in a model of T cell colitis. (A-B) T cell colitis was induced as per FIG. 8A. Starting on day 15 post-transfer, mice were injected with pVAX or PD-L1 c1000 polyplexes weekly for the following 6 weeks via enema or left untreated. Animals that succumbed to disease were given a fixed score of 75% of their initial bodyweight. Injection of PD-L1 polyplexes dampened disease progression as observed by the steady bodyweight throughout the study. (B) Survival curve of mice following the induction of T cell colitis demonstrates that none of the PD-L1 treated animals succumbed to disease. On the other hand, 1 pVAX treated animal and 2 untreated animals had to be euthanized. (C-E) T cell colitis was induced as per FIG. 8A. The bodyweight (C) and clinical signs (D) of the animals were monitored two to three times per week and the bodyweight at day 0 was used as the baseline bodyweight (100%; day 0 is the first day of intra-colonic instillation corresponding to day 19 post-transfer). Animals received weekly intracolonic instillations for 7 weeks starting on day 19 post-transfer. (E) Survival of the mice following the induction of T cell colitis. Animals were euthanized at 75% of their initial bodyweight or if the activity was severely decreased. For graphing purposes, the bodyweight of the euthanized mice was represented as 75% of their initial bodyweight for the remainder of the experiment. Similarly, the clinical score of the euthanized mice was represented as the maximum score of 8 until the termination of the study. For (C-E), Sucrose n=8, pVAX n=9, PD-L1-Fc n=9.
Figure 13B:
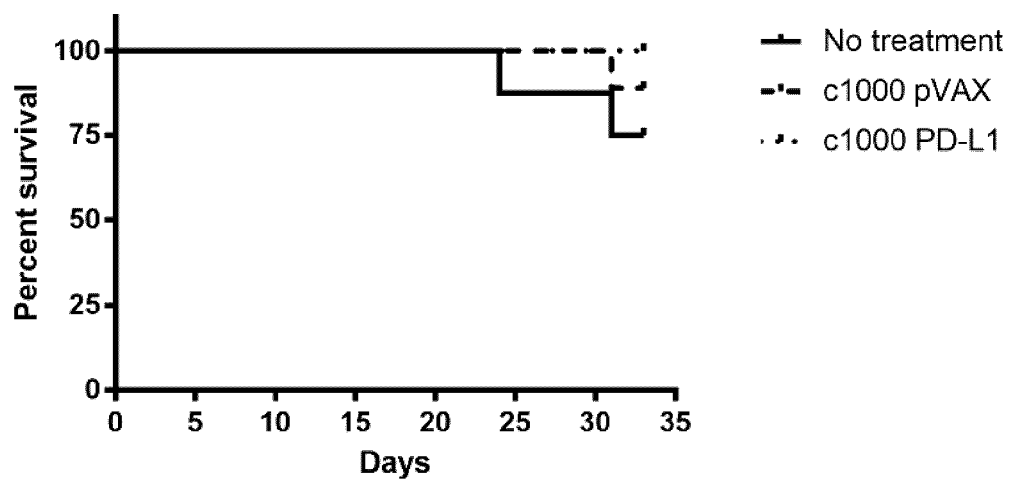
Figure 13C:
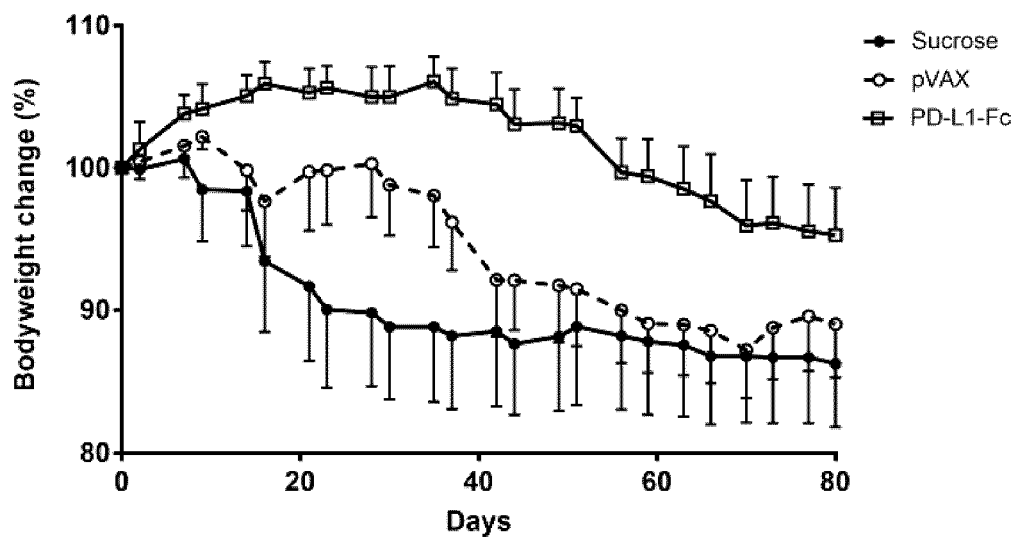
Figure 13D:
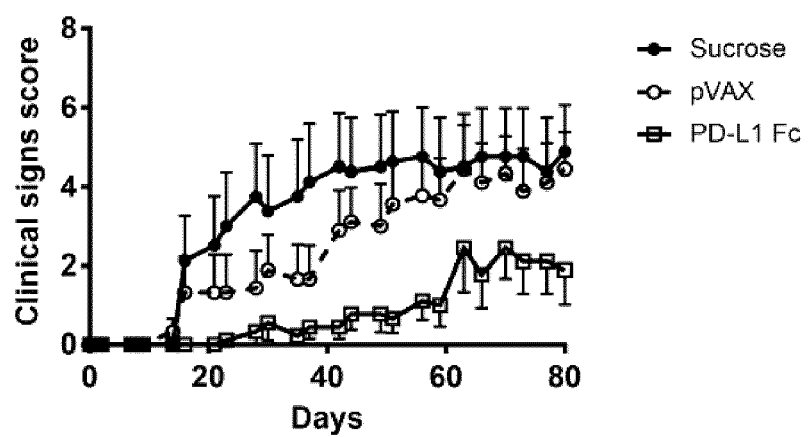
Figure 13E:
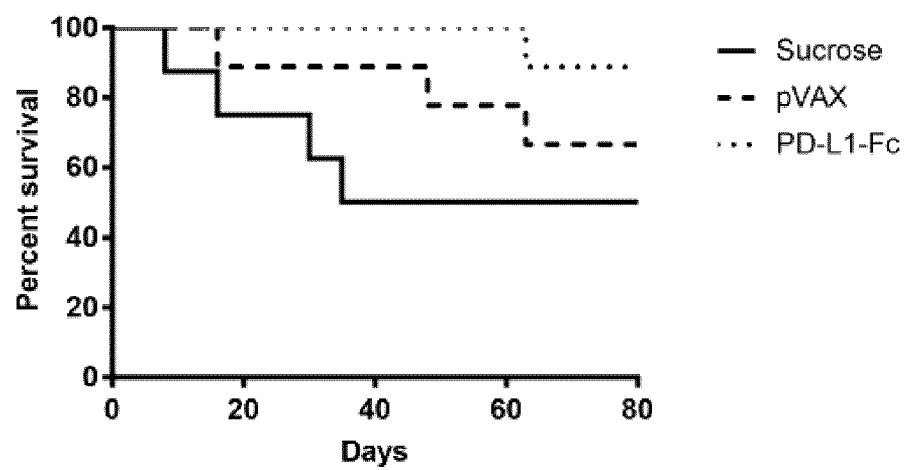
Figure 14A:
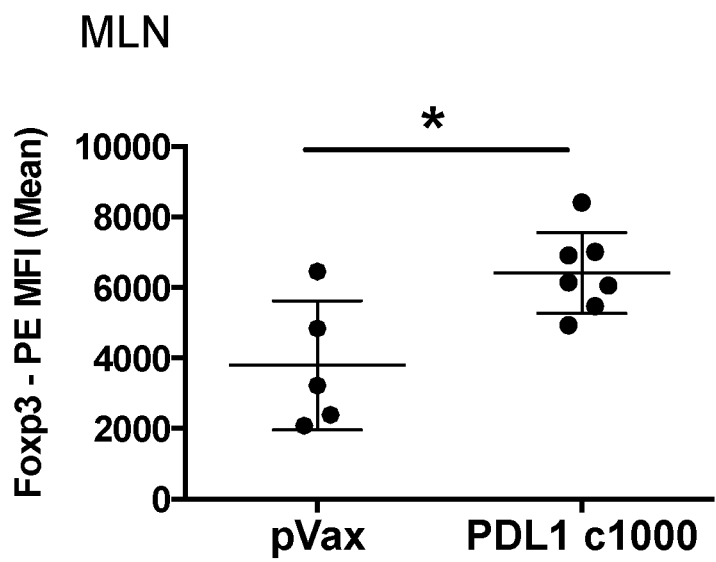
FIG. 14: Administration of PD-L1 polyplex induces the expression of FoxP3 in regulatory T cells. The mean fluorescence intensity (MFI) of FoxP3 was examined in regulatory T cells, defined as CD4+CD25+ FoxP3+ cells, at endpoint in mesenteric lymph nodes and spleen. The expression of FoxP3 was higher in PD-L1 treated animals in both the (A) mesenteric lymph node (MLN) and (B) spleen compared with the pVax group.
Figure 14B:
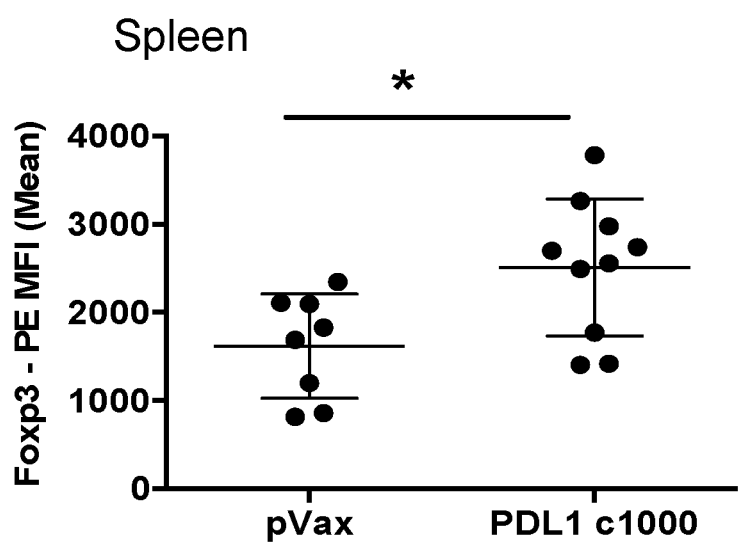

Weekly administration of the PD-L1-Fc polyplex by intracolonic instillation decreased the bodyweight loss and clinical signs of disease in PD-L1-Fc treated mice compared to pVAX and sucrose control mice (FIG. 13C-D). Furthermore, treatment with the PD-L1-Fc polyplex improved the survival of the mice relative to control groups (FIG. 13E).

While the present disclosure has been described with reference to preferred embodiments, it will be understood by those skilled in the art that various changes may be made and equivalents may be substituted for elements thereof to adapt to particular situations without departing from the scope of the present disclosure. Therefore, it is intended that the present disclosure not be limited to the particular embodiments disclosed as the best mode contemplated for carrying out the present disclosure, but that the present disclosure will include all embodiments falling within the scope and spirit of the appended claims.

The invention claimed is:

1. A method for treating an inflammatory disorder in a patient in need thereof, comprising administering to the gastrointestinal tract of said patient an expression vector comprising a programmed death-ligand 1 ("PD-L1") nucleic acid, encoding a human PD-L1 polypeptide, for localized intestinal expression of the human PD-L1 polypeptide,
wherein the expression vector is encapsulated in a chitosan derivative nanoparticle,
wherein the inflammatory disorder is selected from: inflammatory bowel disease, ulcerative colitis, and Crohn's disease, and
wherein said PD-L1 nucleic acid comprises a sequence that is at least about 95% identical to SEQ ID NO: 3 or SEQ ID NO: 4.

2. The method according to claim 1, wherein said PD-L1 polypeptide is a soluble human PD-L1 polypeptide comprising or consisting of the IgV domain and the IgC domain of human PD-L1 (amino acids 19-239 of SEQ ID NO: 1).

3. The method according to claim 1, wherein said PD-L1 polypeptide is a soluble human PD-L1 polypeptide comprising or consisting of the signal sequence, the IgV domain and the IgC domain of human PD-L1 (amino acids 1-239 of SEQ ID NO: 1).

4. The method according to any of claim 1, 2, or 3, wherein the PD-L1 polypeptide is N-terminally fused to a human IgG1 Fc region.

5. The method according to claim 4, wherein said PD-L1 polypeptide is fused to a human IgG1 Fc region via an amino acid sequence of (GGGGS)n (SEQ ID NO: 5).

6. The method according to claim 4, wherein said human IgG1 Fc is mutated to reduce antibody-dependent cellular cytotoxicity (ADCC) and complement-dependent cellular cytotoxicity (CDCC) by altering one or more of the following amino acids in the Fc domain: E233P, L234V, L235A, deletion of G236, A327G, A330S and P331S.

7. The method according to claim 4, wherein said PD-L1 nucleic acid comprises the sequence of SEQ ID NO. 4.

8. The method according to claim 1, wherein said PD-L1 polypeptide is a membrane-bound PD-L1 polypeptide comprising or consisting of the signal sequence, IgV domain, IgC domain and the transmembrane domain of human PD-L1 (amino acids 1-259 of SEQ ID NO: 1).

9. The method according to claim 8, wherein said PD-L1 polypeptide further comprises the cytoplasmic domain of human PD-L1.

10. The method according to claim 9, wherein said PD-L1 nucleic acid comprises the sequence of SEQ ID NO. 3.

11. An expression vector comprising a PD-L1 nucleic acid, wherein said PD-L1 nucleic acid comprises the sequence of SEQ ID NO. 4.

12. An expression vector comprising a PD-L1 nucleic acid, wherein said PD-L1 nucleic acid comprises the sequence of SEQ ID NO. 3.

* * * * *